(12) United States Patent
Katsarava et al.

(10) Patent No.: US 8,445,627 B2
(45) Date of Patent: May 21, 2013

(54) ALKYLENE-DICARBOXYLATE-CONTAINING BIODEGRADABLE POLY(ESTER-AMIDES) AND METHODS OF USE

(75) Inventors: Ramaz Katsarava, Tbilisi (GE); Natia Mazanashvili, Tbilisi (GE); Zaza D. Gomurashvili, La Jolla, CA (US); Turner Daniel Jenkins, San Diego, CA (US); Nino Mchedlishvili, Tbilisi (GE)

(73) Assignee: Medivas, LLC, San Diego, CA (US)

( * ) Notice: Subject to any disclaimer, the term of this patent is extended or adjusted under 35 U.S.C. 154(b) by 0 days.

(21) Appl. No.: 11/728,100

(22) Filed: Mar. 22, 2007

(65) Prior Publication Data

US 2007/0287987 A1 Dec. 13, 2007

Related U.S. Application Data

(60) Provisional application No. 60/785,610, filed on Mar. 24, 2006, provisional application No. 60/840,081, filed on Aug. 25, 2006.

(51) Int. Cl.
*A61K 9/19* (2006.01)

(52) U.S. Cl.
USPC ............. 528/341; 525/218; 528/44; 528/176; 528/179; 528/182; 528/184; 528/292; 528/296; 528/310

(58) Field of Classification Search .................. 528/372, 528/44, 341, 176, 179, 182, 184, 292, 296, 528/310; 525/218
See application file for complete search history.

(56) References Cited

U.S. PATENT DOCUMENTS

| | | | | |
|---|---|---|---|---|
| 5,516,881 A | | 5/1996 | Lee et al. ...................... | 528/320 |
| 5,610,241 A | | 3/1997 | Lee et al. ...................... | 525/411 |
| 5,852,155 A | * | 12/1998 | Bussink et al. ............... | 528/170 |
| 6,352,667 B1 | | 3/2002 | English ..................... | 264/328.17 |
| 6,476,204 B1 | | 11/2002 | Kim et al. ..................... | 536/18.2 |
| 6,503,538 B1 | | 1/2003 | Chu et al. ...................... | 424/497 |
| 7,408,018 B2 | * | 8/2008 | Chu et al. ...................... | 528/341 |
| 2004/0063606 A1 | * | 4/2004 | Chu et al. ......................... | 514/1 |

OTHER PUBLICATIONS

De Simone et al Synthesis, characterization, and degradation of block polyesteramides containing poly(L-lactide) segments, J. Appl. Polym. Sci, vol. 46, pp. 1813-1820 (1992).*
Cohen and Lipowitz, "Acid-Catalyzed Amide Hydrolysis Assisted by a Neighboring Amide Group", *J. Am. Chem. Soc.*, 86:5611, 1964.
Fujimaki, "Processability and properties of aliphatic polyesters, 'BIONOLLE', synthesized by polycondensation reaction", *Polym. Degrad. Stabil.*, 59:209-214, 1998.
Katsarava et al., "Synthesis of high-molecular-weight polysuccinamides by polycondensation of active succinates with diamines", *Makromol. Chem., B.*, 187:2053, 1986.
Shirahama et al., "Synthesis and Enzymatic Degradation of High Molecular Weight Aliphatic Polyesters", *J. AppL Polym. Sci.*, 80:340-347, 2001.
Vigneron et al., "Etude Cinetique de L'hydrolyse des Amides Aliphatiques", *Bull. Soc. Chim. Belg.*, 69:616, 1960.
De Simone et al., "Synthesis, Characterization, and Degradation of Block Polyesteramides Containing Poly (L-Lactide) Segments", *Journal of Applied Polymer Science*, 46:1813-1820 (1992).

* cited by examiner

*Primary Examiner* — Gregory Listvoyb
(74) *Attorney, Agent, or Firm* — Nixon & Vanderhye P.C.

(57) ABSTRACT

The invention provides new aliphatic diester-di-acid-containing PEA polymer compositions with significant improvement in hydrolytic degradation rates as compared to aliphatic di-acid-containing PEA polymers. The di-acids used in the invention PEA compositions include non-toxic fatty aliphatic homologs. These molecules inherently contain two-ester groups, which easily can be cleaved by biotic (enzymatic) and abiotic hydrolysis. Additional di-acid-type compounds useful for active polycondensation are α,ω-alkylene dicarboxylates composed of short aliphatic non toxic diols and di-acids. In addition, the invention PEA polymer compositions optionally can include a second monomer, such as a C-protected L-lysine-based monomer, to introduce additional chain flexibility into the polymer. The invention PEA polymer compositions are useful for delivery of bioactive agents when administered internally.

13 Claims, 4 Drawing Sheets

ALKYLENE-DICARBOXYLATE-CONTAINING BIODEGRADABLE POLY(ESTER-AMIDES) AND METHODS OF USE

RELATED APPLICATIONS

This application claims priority under 35 U.S.C. §119(e) of U.S. Provisional application Ser. Nos. 60/785,610 filed Mar. 24, 2006 and 60/840,081 filed Aug. 25, 2006 each of which is hereby incorporated by reference in its entirety.

FIELD OF THE INVENTION

The invention relates, in general, to drug delivery systems and, in particular, to polymer delivery compositions that incorporate alpha-amino acids and aliphatic diester-di-acids into a biodegradable polymer backbone.

BACKGROUND OF THE INVENTION

Regular AA-BB-type bio-analogous poly(ester amides) (PEAs), consisting of nontoxic building blocks, such as hydrophobic α-amino acids, aliphatic diols and di-carboxylic acids have been proven to be important materials for biomedical applications because of their excellent blood and tissue compatibility (K. DeFife et al. *Transcatheter Cardiovascular Therapeutics—TCT* 2004 *Conference. Poster presentation.* Washington D.C. 2004) and biologic degradation profiles (G. Tsitlanadze, et al. *J. Biomater. Sci. Polymer Edn.* (2004). 15:1-24). Controlled enzymatic degradation and low nonspecific degradation rates of PEAs make them attractive for drug delivery applications.

These properties of PEAs provide advantages over widely used aliphatic polyesters, such as polylactic acid (PLA) and polyglycolic acid (PGA). Aliphatic ester-groups in macromolecules of PLA and PGA contribute to rapid hydrolytic degradation rates, but polymer surfaces are known to display poor adhesion and cell growth, which properties are important indicators of cell-biomaterial interactions (Cook, A D, et al. *J. Biomed. Mater. Res.*, (1997). 35: 513-523).

Due to increased environmental concerns, other aliphatic biodegradable polyesters have also gained renewed interest as an alternative to commodity plastics (Vert M., *J. Macromol. Sci. Pure Appl. Chem. A*. (1995). 32: 787-97 and Mayer J M, Kaplan D L, *Trends Polym. Sci*. (1994). 2: 227-8). Poly (butylene succinate), poly(butylene succinate-adipate) copolymer, and poly(ethylene succinate) have successfully been prepared through condensation reactions of glycols with aliphatic dicarboxylic acids[6] and commercialized under the trade mark of BIONOLLE™. Aliphatic polyesters have been proven to undergo enzymatic hydrolysis by cholesterol esterase, *Rizopus delemaer* lipase and by non-enzymatic hydrolysis (Shirahama H, et al, J. Appl. Polym. Sci. (2001). 80: 340-347).

Among aliphatic di-acids, succinic acid is one of the most attractive building blocks for constructing biocompatible biodegradable polymers since it is a naturally occurring product widely used in the food industry and in perfumery. Derivatives of succinic acid undergo strong intramolecular catalysis due to the 1,2 (vicinal) positions of the acting groups. For example, it is well known (Vigneron B, et al. *Bull. Soc. Chim. Belg.*, (1960). 69: 616 and Cohen T, and Lipowitz J, *J. Am. Chem. Soc*., (1964). 86: 5611) that vicinal amide bonds catalyze the hydrolysis of amide or ester linkages, such as is the case for succinic acid di-amide and ester amide (scheme below).

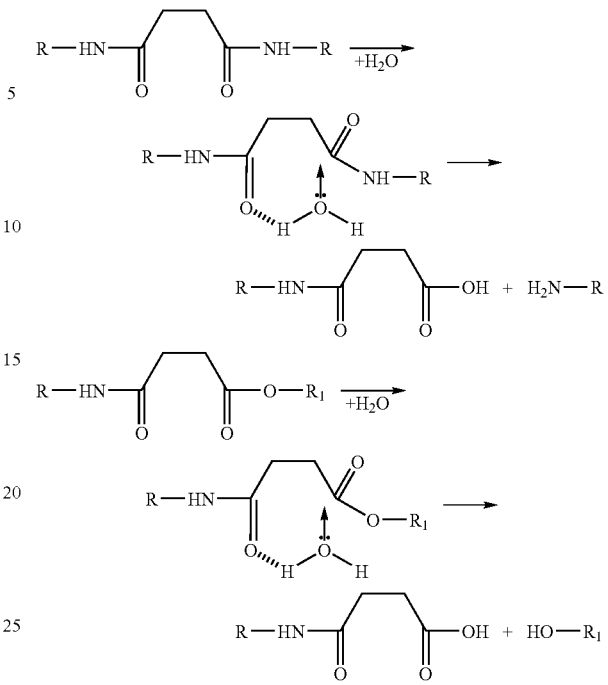

Despite this progress in knowledge of the art, the need exists for new and better polyamides and poly(ester amides), such as those composed of succinic acid as potentially self-degradable polymers.

The synthesis of high-molecular-weight poly(succinic amides) using traditional polycondensation (PC) methods—High Temperature PC (HTPC) in melt or high-boiling organic solvents, and Low Temperature PC (LTPC) in solution or interfacially—is problematic due to extensive chain termination connected with the formation of five-member succinimide cyclization.

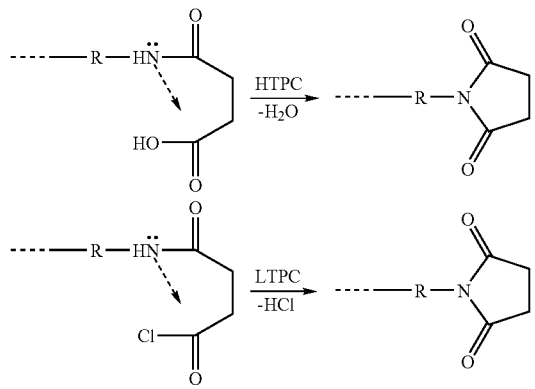

For this reason, high-molecular-weight film-forming polyamides (PAs) were not described in the literature until 1986. Then Katsarava et al. (*Makromol. Chem., B*. (1986). 187: 2053) published an account of the first synthesis of high-molecular-weight poly(succinamides) obtained by interaction of active succinates with diamines (free bases) under mild conditions using solution active polycondensation (APC).

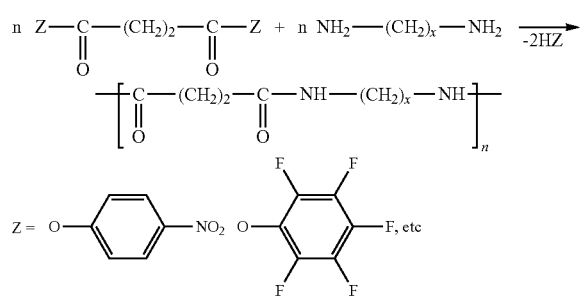

Application of this approach to the synthesis of amino acid-based poly(ester amides) using di-p-toluene sulfonic acid salts instead of free diamines, however, yielded low molecular weight poly(ester amides) that form brittle films. This result could be attributed to the necessity of using relatively harsh reaction conditions (e.g., 80° C.), which are favorable for cyclization and may cause some imide formation, although to a lesser extent than in HTPC and LTPC. However, extent of cyclization was high enough to result in chain termination, which resulted in decreased molecular weights of the PEAs. This result was attributed to the fact that, after interaction of one ester group in the active succinate, the additional ester groups present, which are as active as the first one, can participate in a cycle-forming (chain termination) reaction in parallel with an aminolysis (chain growth) reaction.

In the early eighties, Tsamantakis et al. (*Angew. Makrom. Chem.* (1982) 104: 19-30) described diester-di-acid type new monomers and their active di-(p-nitrophenyl) esters. In these studies, alkylene-dicarboxylate monomer syntheses involved succinic or glutaric acids and α,ω-diols. Bis-succinates or bis-glutarates of diols successfully polycondensed with aliphatic or aromatic diamines to yield polymers with moderate to high (up to 1.76 dL/g) inherent viscosities. However, the resulting degradable polymers contained toxic diamines, limiting their potential for biomedical application.

Therefore, the need exists for new and better methods for synthesis of alkylene-dicarboxylate-containing biocompatible and biodegradable poly(ester-amides) (PEAs), compositions containing such PEAs, and methods of their use. The need also exists for new alkylene dicarboxylates for use in making such PEA compositions.

SUMMARY OF THE INVENTION

The present invention is based on the discovery of new aliphatic diester-di-acid-containing PEA polymer compositions with significant improvement in hydrolytic degradation rates as compared to aliphatic di-acid-containing PEA polymers. Bis(α-amino acid)-α,ω-alkylene-diester is a type of diamine monomer, useful for active polycondensation (APC), and which inherently contains two aliphatic ester linkages. Such ester groups can be enzymatically recognized by various esterases. Condensation of diamine monomers, for example, with activated di-acid esters, results in a PEA macromolecule with ester and amide functionalities. The di-acids used in the invention PEA compositions include non-toxic fatty aliphatic homologs. Additional di-acid-type compounds useful for active polycondensation according to the present invention are α,ω-alkylene dicarboxylates of formula (III) below, composed of short aliphatic non toxic diols and di-acids.

These molecules inherently contain two-ester groups, which easily can be cleaved by biotic (enzymatic) and abiotic hydrolysis. The invention PEA polymer compositions possess an increased number of ester groups in the elemental chain unit as compared with previously known PEA polymers, which ester groups confer more rapid biodegradability than polymers composed of aliphatic di-acids with alkylene chains. In addition, the invention PEA polymer compositions optionally can include a second, C-protected L-lysine-based monomer to introduce additional chain flexibility into the polymer.

Accordingly in one embodiment, the invention provides biodegradable polymer compositions comprising a PEA polymer having a chemical formula described by general structural formula (I), Formula (I)

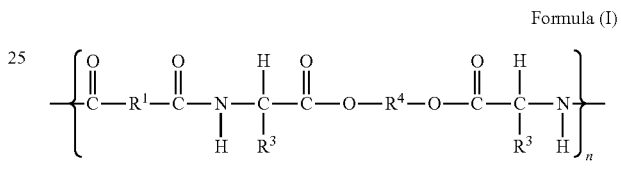

wherein n ranges from about 5 to about 150; $R^1$ is independently selected from residues of α,ω-alkylene dicarboxylates of formula (III) below, or in combination with ($C_2$-$C_{20}$) alkylene, ($C_2$-$C_{20}$) alkenylene, α,ω-bis(4-carboxyphenoxy)-($C_1$-$C_8$) alkane, 3,3'-(alkanedioyldioxy)dicinnamic acid or 4,4'-(alkanedioyldioxy)dicinnamic acid, or saturated or unsaturated residues of therapeutic di-acids; and wherein $R^5$ and $R^6$ in Formula (III) are independently selected from ($C_2$-$C_{12}$) alkylene or ($C_2$-$C_{12}$) alkenylene; the $R^3$s in individual n units are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl, and —$(CH_2)_2SCH_3$; and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), saturated or unsaturated therapeutic diol residues, and combinations thereof;

Formula (II)

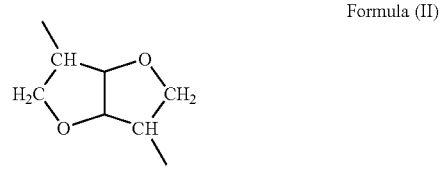

Formula (III)

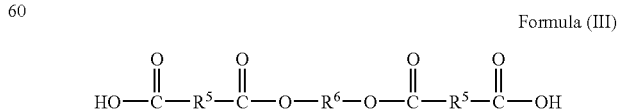

or a PEA polymer having a chemical formula described by structural formula (IV):

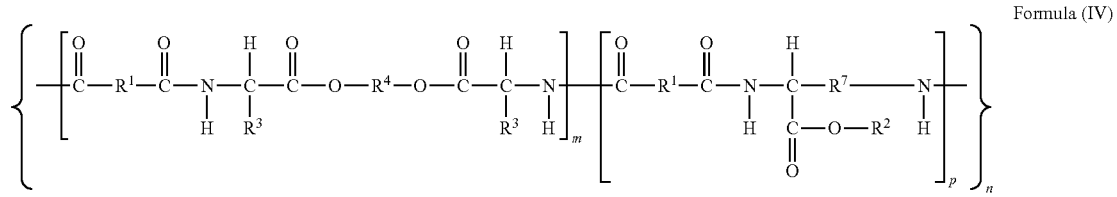

Formula (IV)

wherein n ranges from about 5 to about 150, m ranges about 0.1 to 0.9; p ranges from about 0.9 to 0.1; $R^1$ is independently selected from residues of α,ω-alkylene dicarboxylates of structural formula (III), or in combination with ($C_2$-$C_{20}$) alkylene and ($C_2$-$C_{20}$) alkenylene, α,ω-bis(4-carboxyphenoxy)-($C_1$-$C_8$) alkane, 3,3'-(alkanedioyldioxy) dicinnamic acid, 4'-(alkanedioyldioxy)dicinnamic acid, or saturated or unsaturated residues of therapeutic di-acids; and wherein $R^5$ and $R^6$ in Formula (III) are independently selected from ($C_2$-$C_{12}$) alkylene or ($C_2$-$C_{12}$) alkenylene; each $R^2$ is independently hydrogen, ($C_1$-$C_{12}$) alkyl, ($C_6$-$C_{10}$) aryl or a protecting group; the $R^3$s in individual m monomers are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl, and —$(CH_2)_2SCH_3$; and $R^4$ is independently selected from the group consisting of ($C_2$-$C_{20}$) alkylene, ($C_2$-$C_{20}$) alkenylene, ($C_2$-$C_8$) alkyloxy, ($C_2$-$C_{20}$) alkylene, bicyclic-fragments of 1,4:3,6-dianhydrohexitols of structural formula (II), residues of saturated or unsaturated therapeutic diols and combinations thereof; $R^7$ is independently ($C_2$-$C_{20}$) alkyl or ($C_2$-$C_{20}$) alkenyl In another embodiment the invention provides surgical devices comprising the invention PEA polymer.

In still another embodiment, the invention provides methods for preparing an alkylene-dicarboxylate having a chemical formula described by structural formula (III), wherein $R^5$ and $R^6$ are independently selected from ($C_2$-$C_{12}$) alkylene, ($C_2$-$C_{12}$) alkenylene, and wherein the $R^5$ is contained in a cyclic aliphatic five, six or seven-member anhydride, and the $R^6$ is contained in a diol, by interacting the diol with the anhydride in the presence of a suitable solvent and catalyst.

In yet another embodiment, the invention provides compounds having a chemical structure described by structural formula (III), wherein $R^5$ is selected from $(CH_2)_2$, $(CH_2)_3$, or CH=CH; and $R^6$ is selected from $(CH_2)_3$, $(CH_2)_4$, $(CH_2)_6$, or $(CH_2)_8$.

A BRIEF DESCRIPTION OF THE FIGURES

FIG. 3 is a graph showing the FTIR spectra of a film of invention PEA polymer (Compound 3.2 of Table 3).

DETAILED DESCRIPTION OF THE INVENTION

Figure 1:
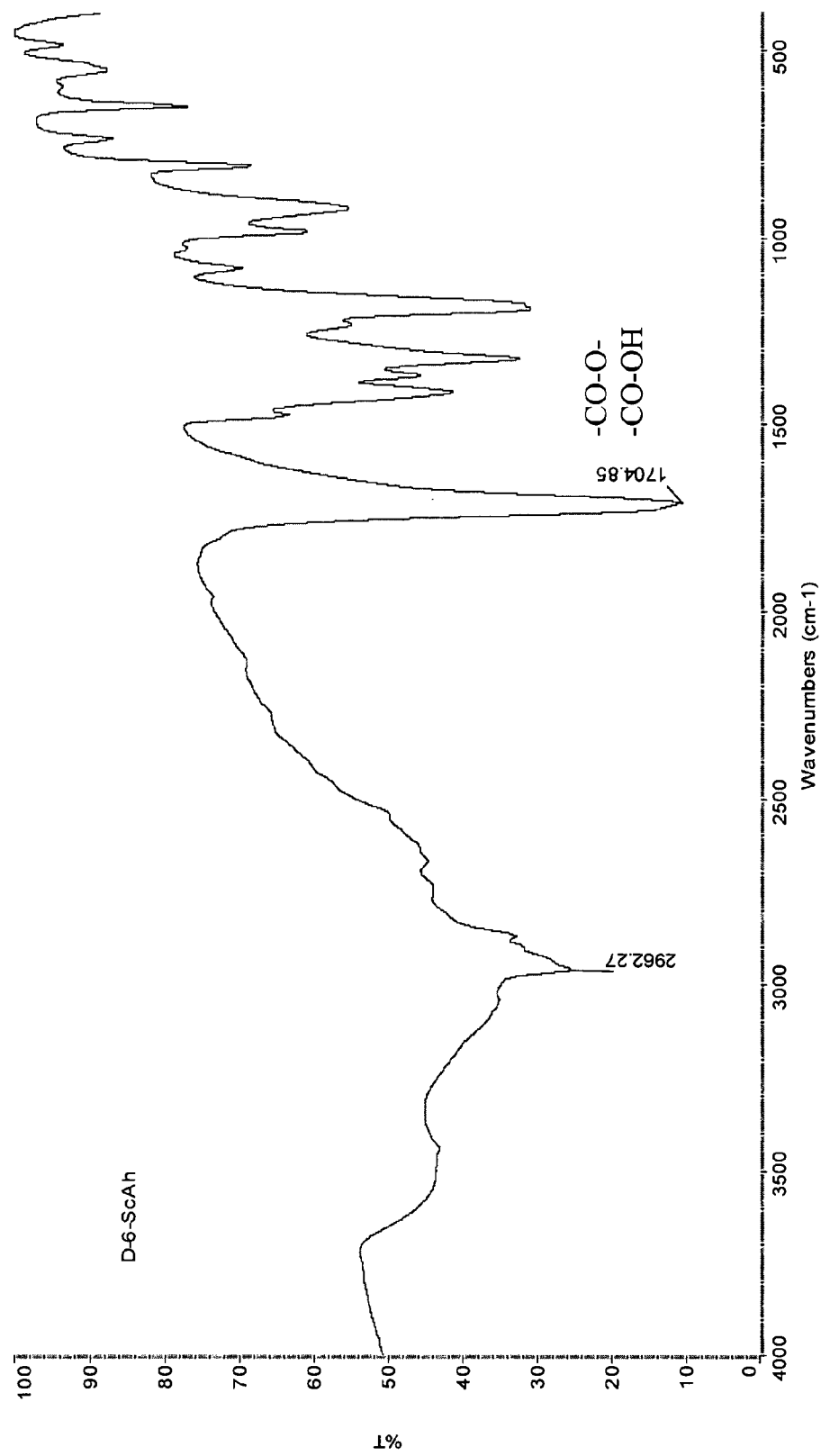
FIG. 1 is a graph showing the FTIR spectrum of 1,6-hydroxyhexyl disuccinate, (Compound 1.1 of Table 1, wherein $R^5$=$(CH_2)_2$, and $R^6$=$(CH_2)_6$.

The present invention is based on the discovery of new aliphatic di-acid-containing PEA polymer compositions with significant improvement in hydrolytic degradation rates as compared to non-aliphatic di-acid-containing PEA polymers. As the aliphatic di-acids using in making the invention PEA polymers inherently contain two-ester groups, the polymers easily can be cleaved by biotic (enzymatic) and abiotic hydrolysis. The invention PEA polymer compositions possess an increased number of ester groups in the elemental chain unit as compared with previously known PEA polymers, which ester groups confer more rapid biodegradability than polymers composed of aliphatic di-acids with alkylene chains. In addition, the invention PEA polymer compositions optionally can include a second monomer, such as a C-protected L-lysine-based monomer, to introduce additional chain flexibility into the polymer.

Accordingly in one embodiment, the invention provides biodegradable polymer compositions comprising at least one or a blend of PEA polymers having a chemical formula described by general structural formula (I),

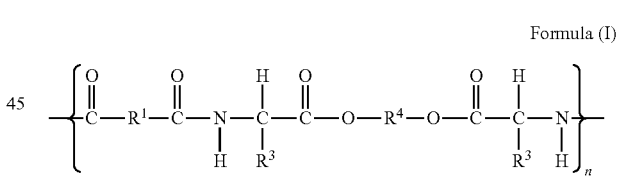

Formula (I)

wherein n ranges from about 5 to about 150; $R^1$ is independently selected from residues of α,ω-alkylene dicarboxylates of formula (III) below, or in combination with ($C_2$-$C_{20}$) alkylene, ($C_2$-$C_{20}$) alkenylene, α,ω-bis(4-carboxyphenoxy)-($C_1$-$C_8$) alkane, 3,3'-(alkanedioyldioxy)dicinnamic acid or 4,4'-(alkanedioyldioxy)dicinnamic acid, or saturated or unsaturated residues of therapeutic di-acids; and wherein $R^5$ and $R^6$ in Formula (III) are independently selected from ($C_2$-$C_{12}$) alkylene or ($C_2$-$C_{12}$) alkenylene; the $R^3$s in individual n units are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl, and —$(CH_2)_2SCH_3$; and $R^4$ is independently selected from the group consisting of ($C_2$-$C_{20}$) alkylene, ($C_2$-$C_{20}$) alkenylene, ($C_2$-$C_8$) alkyloxy, ($C_2$-$C_{20}$) alkylene, bicyclic-fragments of 1,4:3,6-dianhydrohexitols of structural formula (II), saturated or unsaturated therapeutic diol residues, and combinations thereof;

Formula (II)

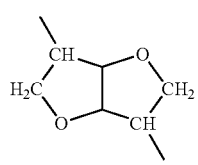

Formula (III)

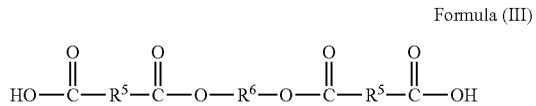

or a PEA polymer having a chemical formula described by structural formula (IV):

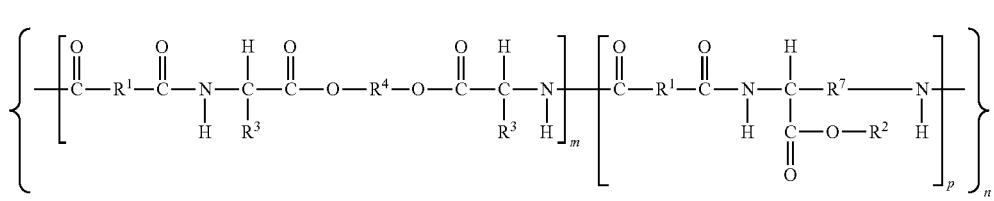

Formula (IV)

wherein n ranges from about 5 to about 150, m ranges about 0.1 to 0.9; p ranges from about 0.9 to 0.1; $R^1$ is independently selected from residues of α,ω-alkylene dicarboxylates of structural formula (III), or in combination with ($C_2$-$C_{20}$) alkylene and ($C_2$-$C_{20}$) alkenylene, α,ω-bis(4-carboxyphenoxy)-($C_1$-$C_8$) alkane, 3,3'-(alkanedioyldioxy)dicinnamic acid, 4'-(alkanedioyldioxy)dicinnamic acid, or saturated or unsaturated residues of therapeutic di-acids;

wherein $R^5$ and $R^6$ in Formula (III) are independently selected from ($C_2$-$C_{12}$) alkylene, ($C_2$-$C_{12}$) alkenylene, and combinations thereof; each $R^2$ is independently hydrogen, ($C_1$-$C_{12}$) alkyl, ($C_6$-$C_{10}$) aryl or a protecting group; the $R^3$s in individual m monomers are independently selected from the group consisting of hydrogen, ($C_1$-$C_6$) alkyl, ($C_2$-$C_6$) alkenyl, ($C_2$-$C_6$) alkynyl, ($C_6$-$C_{10}$) aryl ($C_1$-$C_6$) alkyl, and —($CH_2$)$_2$SCH$_3$; and $R^4$ is independently selected from the group consisting of ($C_2$-$C_{20}$) alkylene, ($C_2$-$C_{20}$) alkenylene, ($C_2$-$C_8$) alkyloxy ($C_2$-$C_{20}$) alkylene, bicyclic-fragments of 1,4:3,6-dianhydrohexitols of structural formula (II), residues of saturated or unsaturated therapeutic diols and combinations thereof; and $R^7$ is independently ($C_2$-$C_{20}$) alkyl or ($C_2$-$C_{20}$) alkenyl. Preferably, $R^7$ is ($C_3$-$C_6$) alkyl or ($C_3$-$C_6$) alkenyl; most preferably —($CH_2$)$_4$—

When in a PEA of structural formula (I), $R^1$ is equal to Formula (III), then the PEA will have the chemical structure described by structural Formula (V);

A typical protecting group for use in the invention polymers is t-butyl, or others as are known in the art. The bicyclic-fragments of 1,4:3,6-dianhydrohexitols can be derived from "sugar alcohols", such as D-glucitol, D-mannitol, or L-iditol, for example isosorbide (1,4:3,6-dianhydrosorbitol).

The chemical formula of the class of α,ω-alkylene di-acids useful in the practice of the invention is described by structural formula (III), wherein, $R^5$ and $R^6$ can be independently selected from ($C_2$-$C_{12}$) alkylene or ($C_2$-$C_{12}$) alkenylene. In one embodiment, $R^5$ can be selected from $C_2$-$C_4$ alkylene, or $C_2$-$C_4$ alkenylene and $R^6$ can be selected from ($C_2$-$C_8$) alkylene.

Known examples of di-acids of α,ω-alkylene dicarboxylates of formula (III) suitable for use in practice of the invention include 1,4-hydroxybutyl disuccinate (where $R^5$=(CH$_2$)$_2$, $R^6$=(CH$_2$)$_4$), 1,3-hydroxypropyl dimalonate (where $R^5$=(CH=CH), $R^6$=(CH$_2$)$_3$, and 1,6-hydroxyhexyl diglutarate (where $R^5$=(CH$_2$)$_3$, $R^6$=(CH$_2$)$_6$).

The n monomers in the invention PEA polymers of structural formula (I, or V) can be identical, in which case the polymer is referred to herein as a "homo-polymer." Alternatively, the n monomers in the invention PEA polymers of structure (I) can be different, being fabricated using different combinations of building blocks (i.e., diols, di-acids and α-amino acids), in which case the polymer is referred to herein as a "co-polymer". The m-monomers in the invention PEA polymers of structure (IV), which include an L-lysine-based monomer p, can be either identical or different.

As used herein, the term "residue of a di-acid" means a portion of a dicarboxylic-acid, as described herein, that excludes the two carboxyl groups of the di-acid. As used herein, the term "residue of a diol" means a portion of a diol, as described herein, which excludes the two hydroxyl groups of the diol. The corresponding di-acid or diol containing the "residue" thereof is used in synthesis of the co-polymer compositions. The residue of the di-acid or diol is reconstituted in vivo (or under similar conditions of pH, aqueous media, and the like) to the corresponding diol or di-acid upon release from the polymer composition by biodegradation in a controlled manner that depends upon the properties of the α,ω-bis(4-carboxyphenoxy)alkane-containing polymer used in the composition, which properties are as described herein, for example in the Examples.

As used herein, the terms "α-amino acid-containing", and "α-amino acid" mean a chemical compound containing an amino group, a carboxyl group and an $R^3$ group as defined

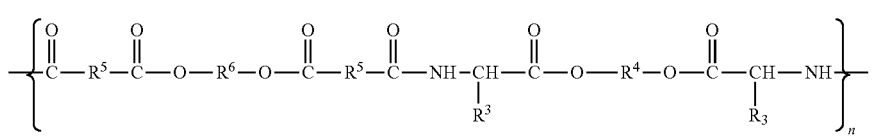

Formula (V)

herein. As used herein, the terms "biological α-amino acid-containing" and "biological α-amino acid" mean the α-amino acid(s) used in synthesis is phenylalanine, leucine, glycine, alanine, valine, isoleucine, methionine, or a mixture thereof As used herein the term "bioactive agent" means a bioactive agent as disclosed herein that is not incorporated into the polymer backbone, but is dispersed within the alkylene di-acid containing PEA polymer. One or more such bioactive agents may optionally be included in the invention polymer compositions. As used herein, the term "dispersed" as used to refer to bioactive agents, means the bioactive agents are dispersed, mixed, dissolved, homogenized, and/or covalently bound ("dispersed") in an invention polymer composition, for example attached to a functional group in the PEA polymer of the composition or to the surface of a polymer particle or medical device made using the invention PEA polymer composition.

Use of a residue of a saturated or unsaturated alkyl diol in the monomers provides elongation properties of the resulting polymer. A second, L-lysine-based monomer optionally can be included in an invention polymer to introduce an additional diol residue that can be selected to further control the thermo-mechanical properties of the polymer.

The biodegradable polymers containing unsaturated groups have potential for various applications. For example, unsaturated groups can be converted into other functional groups such as epoxy or alcohol—useful for further modifications. Their crosslinking could enhance thermal and mechanical properties of polymer.

The invention alkylene di-acid-containing PEA polymers exhibit a combination of hydrophobicity, relatively high glass transition temperature (Tg) to confer sufficient stiffness for the polymers to be extruded, and sufficient elongation properties to prevent brittleness. In certain embodiments, individual monomer units in the invention alkylene di-acid-containing PEA polymer compositions can be based on and break down during biodegradation to yield one of multiple different α-amino acids, as disclosed herein.

Like other PEA polymers, the invention alkylene di-acid-containing PEA polymer compositions can be used to deliver in vivo at least one bioactive agent that is dispersed in the polymer of the composition. The invention PEA polymer compositions biodegrade in vivo by enzymatic action so as to release the at least one bioactive agent(s) from the polymer in a controlled manner over time. Thus the invention provides new PEA polymers suitable for certain applications requiring a combination of hydrophobicity, relatively high glass transition temperature (Tg<37° C.), and elongation or flexibility properties. Moreover, since theoretically the bis(α-amino acid)-diol-diester co-monomers in the invention PEA polymers may each contain a different one of the multiple amino acids disclosed herein in each bis(α-amino acid) building block, the invention PEA polymer compositions may break down to produce from one to multiple different of such α-amino acids.

The terms, "biodegradable and biocompatible" as used herein to describe the invention PEA polymer compositions means the polymer is capable of being broken down into innocuous products in the normal functioning of the body. This is particularly true when the amino acids used in fabrication of the PEA polymers are biological L-α-amino acids. These PEA polymer compositions include ester groups hydrolyzable by esterases and enzymatically cleavable amide linkages that provide biodegradability, and are typically chain terminated, predominantly with amino groups. Optionally, the amino termini of the polymers can be acetylated or otherwise capped by conjugation to any other acid-containing, biocompatible molecule, to include without restriction organic acids, bioinactive biologics, and bioactive agents as described herein. In one embodiment, the entire polymer composition, and any particles, or medical device made thereof, is substantially biodegradable.

In one alternative, the $R^3$s in at least one n monomer are $CH_2Ph$ and the α-amino acid used in synthesis is L-phenylalanine. In alternatives wherein the $R^3$s within a monomer are —$CH_2$—$CH(CH_3)_2$, the polymer contains the α-amino acid, leucine. By varying the $R^3$s, other α-amino acids can also be used, e.g., glycine (when the $R^3$s are —H), alanine (when the $R^3$s are —$CH_3$), valine (when the $R^3$s are —$CH(CH_3)_2$), isoleucine (when the $R^3$s are —$CH(CH_3)$—$CH_2$—$CH_3$), phenylalanine (when the $R^3$s are —$CH_2$—$C_6H_5$); lysine (when the $R^3$s are —$(CH_2)_4$—$NH_2$); or methionine (when the $R^3$s are —$(CH_2)_2S(CH_3)_2$).

In yet a further embodiment wherein the polymer is a PEA, PEUR or PEU of formula I or IV, at least one of the $R^3$s further can be —$(CH_2)_3$— wherein the $R^3$s cyclize to form the chemical structure described by structural formula (XIV):

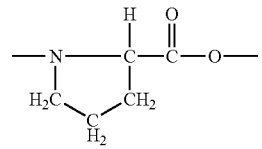

Formula (XIV)

When the $R^3$s are —$(CH_2)_3$—, an α-imino acid analogous to pyrrolidine-2-carboxylic acid (proline) is used.

The term "aryl" is used with reference to structural formulas herein to denote a phenyl radical or an ortho-fused bicyclic carbocyclic radical having about nine to ten ring atoms in which at least one ring is aromatic. In certain embodiments, one or more of the ring atoms can be substituted with one or more of nitro, cyano, halo, trifluoromethyl, or trifluoromethoxy. Examples of aryl include, but are not limited to, phenyl, naphthyl, and nitrophenyl.

The term "alkenylene" is used with reference to structural formulas herein to mean a divalent branched or unbranched hydrocarbon chain containing at least one unsaturated bond in the main chain or in a side chain.

Further, the alkylene di-acid-containing PEA polymer compositions suitable for use in the practice of the invention bear functionalities that allow the option of covalent attachment of bioactive agent(s) to the polymer. For example, a polymer bearing free carboxyl groups can readily react with an amino moiety, thereby covalently bonding a peptide to the polymer via the resulting amide group. As will be described herein, the biodegradable polymer and a bioactive agent may contain numerous complementary functional groups that can be used to covalently attach the bioactive agent to the biodegradable polymer.

Further examples of PEA polymers related to those contemplated for use in the practice of the invention and methods of synthesis include those set forth in U.S. Pat. Nos. 5,516, 881; 5,610,241; 6,476,204; and 6,503,538; and in U.S. application Ser. Nos. 10/096,435; 10/101,408; 10/143,572; 10/194,965 and 10/362,848.

In certain embodiments, particles or a medical device made from or containing the invention alkylene di-acid-containing PEA polymer composition, as described herein, plays an active role in the treatment processes at the site of implant or use by holding the polymer and any bioactive agents dispersed therein at the site for a period of time sufficient to allow the subject's endogenous processes to slowly release particles or polymer molecules from the composition. Meanwhile, the subject's endogenous processes biodegrade the polymer so as to release bioactive agents dispersed in the polymer. The fragile optional bioactive agents are protected by the more slowly biodegrading polymer to increase half-life and persistence of the bioactive agent(s) locally at the site of use, e.g., implant.

Uptake of the polymer with bioactive agent is safe: studies have shown that the subject can metabolize/clear the polymer degradation products. The invention alkylene di-acid-containing PEA polymer compositions are, therefore, substantially non-inflammatory to the subject both at the site of implant and systemically, apart from any trauma caused by implantation itself.

Methods for making PEA polymers containing α-amino acids in the general formula are well known in the art. For example, for the embodiment of the polymer of formula (I), a α-amino acid can be converted into a bis(α-amino acid)-diol-diester monomer, for example, by condensing the α-amino acid with a diol as described herein. As a result, ester bonds are formed. Then, the bis(α-amino acid)-diol-diester is entered into a polycondensation reaction with a di-acid, such as sebacic acid, or α,ω-bis(4-carboxyphenoxy) alkanoic di-acid, to obtain the final polymer having both ester and amide bonds. Alternatively, instead of the di-acid, an activated di-acid derivative, e.g., di-(p-nitrophenyl) ester, can be used for polymers of chemical structure (I).

More particularly, synthesis of the unsaturated poly(ester-amide)s (UPEAs) useful as biodegradable polymers of the structure (I) or (IV) as described above will be described wherein:

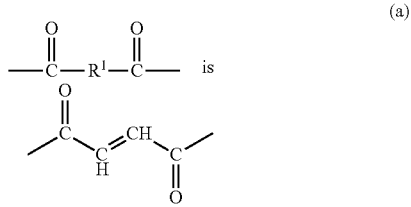

for example, and/or (b) $R^3$ is —$CH_2$—$CH$=$CH$—$CH_2$—. In cases where (a) is present and (b) is not present, $R^3$ can be —$C_4H_8$— or —$C_6H_{12}$—. In cases where (a) is not present and (b) is present, $R^1$ can be —$C_4H_8$— or —$C_8H_{16}$—.

The UPEAs can be prepared by solution polycondensation of either (1) di-p-toluene sulfonic acid salt of bis(α-amino acid) diesters, comprising at least 1 double bond in the diol residue, a di-p-toluene sulfonic acid salt of a bis(α-amino acid)-alkylene-diesters, comprising a diol of structural formula (III), and di-(p-nitrophenyl) esters of saturated dicarboxylic acid or (2) two di-p-toluene sulfonic acid salt of bis(α-amino acid) alkylene-diesters, comprising no double bonds in the diol residues, and di-(p-nitrophenyl) ester of unsaturated dicarboxylic acid or (3) two di-p-toluene sulfonic acid salts of bis (α-amino acid)-diol-diesters, comprising at least one double bond in one of the diol residues in the polymer general structural formula, the other diol residue having structural formula (III), and di-nitrophenyl esters of unsaturated dicarboxylic acids.

Salts of p-toluene sulfonic acid are known for use in synthesizing polymers containing amino acid residues. The aryl sulfonic acid salts are used instead of the free base because the aryl sulfonic salts of bis(α-amino acid)-alkylene-diesters are easily purified through recrystallization and render the amino groups as stable ammonium tosylates throughout workup. In the polycondensation reaction, the nucleophilic amino group is readily revealed through the addition of an organic base, such as triethylamine, so the polymer product is obtained in high yield.

For unsaturated polymers of structure (I, IV or V), the di-(p-nitrophenyl) esters of unsaturated dicarboxylic acid can be synthesized from p-nitrophenol and unsaturated dicarboxylic acid chloride, e.g., by dissolving triethylamine and p-nitrophenol in acetone and adding unsaturated dicarboxylic acid chloride dropwise with stirring at −78° C. and pouring into water to precipitate product. Suitable acid chlorides included fumaric, maleic, mesaconic, citraconic, glutaconic, itaconic, ethenyl-butanedioic and 2-propenyl-butanedioic acid chlorides.

Suitable therapeutic diol compounds that can be used to prepare bis(α-amino acid) diesters of therapeutic diol monomers, or bis(carbonate) of therapeutic di-acid monomers, for introduction into the invention compositions include naturally occurring therapeutic diols, such as 17-β-estradiol, a natural and endogenous hormone, useful in preventing restenosis and tumor growth (Yang, N. N., et al. Identification of an estrogen response element activated by metabolites of 17-β-estradiol and raloxifene. *Science* (1996) 273, 1222-1225; Parangi, S., et al., Inhibition of angiogenesis and breast cancer in mice by the microtubule inhibitors 2-methoxyestradiol and taxol, *Cancer Res*. (1997) 57, 81-86; and Fotsis, T., et al., The endogenous oestrogen metabolite 2-methoxyoestradiol inhibits angiogenesis and suppresses tumor growth. *Nature* (1994) 368, 237-239). The safety profiles of such endogenously occurring therapeutic diol molecules are believed to be superior to those of synthetic and/or non-endogenous molecules having a similar utility, such as sirolimus.

Incorporation of a therapeutic diol into the backbone of a PEA polymer can be accomplished, for example, using active steroid hormone 17-β-estradiol containing mixed hydroxyls—secondary and phenolic. When the PEA polymer is used to fabricate particles and the particles are implanted into a patient, for example, following percutaneous transluminal coronary angioplasty (PTCA), 17-β-estradiol released from the particles in vivo can help to prevent post-implant restenosis in the patient. 17-β-estradiol, however, is only one example of a diol with therapeutic properties that can be incorporated in the backbone of a PEA polymer in accordance with the invention. In one aspect, any bioactive steroid-diol containing primary, secondary or phenolic hydroxyls can be used for this purpose. Many steroid esters that can be made from bioactive steroid diols for use in the invention are disclosed in European application EP 0127 829 A2.

Due to the versatility of the PEA polymers used in the invention compositions, the amount of the therapeutic diol or di-acid incorporated in the polymer backbone can be controlled by varying the proportions of the building blocks of the polymer. For example, depending on the composition of the PEA, loading of up to 40% w/w of 17-β-estradiol can be achieved. Two different regular, linear PEAs with various loading ratios of 17-β-estradiol are illustrated in Scheme 1 below:

Scheme 1

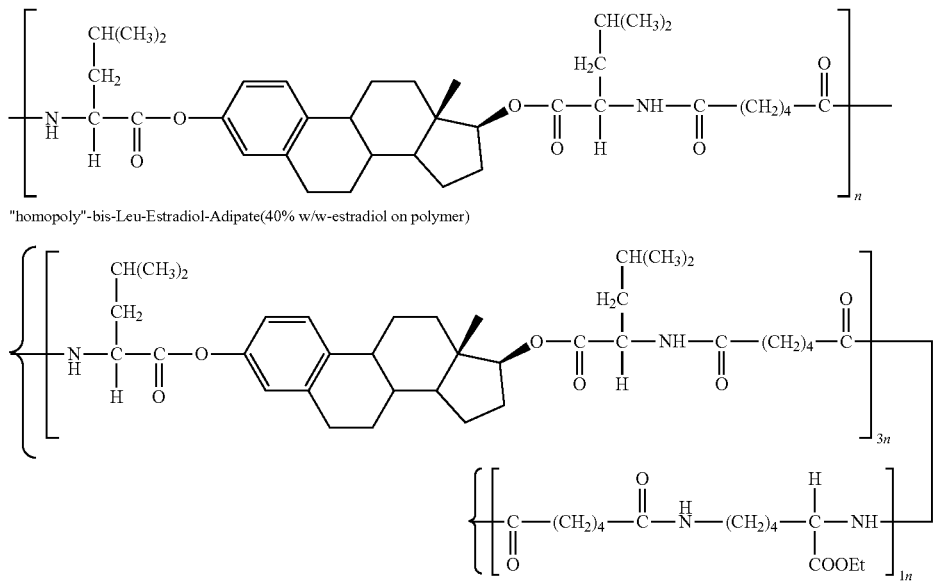

"homopoly"-bis-Leu-Estradiol-Adipate(40% w/w-estradiol on polymer)

Copolymer: Leu(ED)$_3$Lys(OEt)Adip$_4$, with 38% w/w estradiol loading

Similarly, the loading of the therapeutic diol into the polymer can be varied by varying the amount of two or more building blocks of the polymer.

In addition, synthetic steroid based diols based on testosterone or cholesterol, such as 4-androstene-3,17 diol (4-Androstenediol), 5-androstene-3,17 diol (5-Androstenediol), 19-nor5-androstene-3,17 diol (19-Norandrostenediol) are suitable for incorporation into the backbone of PEA polymers according to this invention. Moreover, therapeutic diol compounds suitable for use in preparation of the invention polymer compositions include, for example, amikacin; amphotericin B; apicycline; apramycin; arbekacin; azidamfenicol; bambermycin(s); butirosin; carbomycin; cefpiramide; chloramphenicol; chlortetracycline; clindamycin; clomocycline; demeclocycline; diathymosulfone; dibekacin, dihydrostreptomycin; dirithromycin; doxycycline; erythromycin; fortimicin(s); gentamycin(s); glucosulfone solasulfone; guamecycline; isepamicin; josamycin; kanamycin(s); leucomycin(s); lincomycin; lucensomycin; lymecycline; meclocycline; methacycline; micronomycin; midecamycin(s); minocycline; mupirocin; natamycin; neomycin; netilmicin; oleandomycin; oxytetracycline; paromycin; pipacycline; podophyllinic acid 2-ethylhydrazine; primycin; ribostamycin; rifamide; rifampin; rafamycin SV; rifapentine; rifaximin; ristocetin; rokitamycin; rolitetracycline; rasaramycin; roxithromycin; sancycline; sisomicin; spectinomycin; spiramycin; streptomycin; teicoplanin; tetracycline; thiamphenicol; theiostrepton; tobramycin; trospectomycin; tuberactinomycin; vancomycin; candicidin(s); chlorphenesin; dermostatin(s); filipin; fungichromin; kanamycin(s); leucomycins(s); lincomycin; lvcensomycin; lymecycline; meclocycline; methacycline; micronomycin; midecamycin(s); minocycline; mupirocin; natamycin; neomycin; netilmicin; oleandomycin; oxytetracycline; paramomycin; pipacycline; podophyllinic acid 2-ethylhydrazine; priycin; ribostamydin; rifamide; rifampin; rifamycin SV; rifapentine; rifaximin; ristocetin; rokitamycin; rolitetracycline; rosaramycin; roxithromycin; sancycline; sisomicin; spectinomycin; spiramycin; strepton; otbramycin; trospectomycin; tuberactinomycin; vancomycin; candicidin(s); chlorphenesin; dermostatin(s); filipin; fungichromin; meparticin; mystatin; oligomycin(s); erimycinA; tubercidin; 6-azauridine; aclacinomycin(s); ancitabine; anthramycin; azacitadine; bleomycin(s) carubicin; carzinophillin A; chlorozotocin; chromomcin(s); doxifluridine; enocitabine; epirubicin; gemcitabine; mannomustine; menogaril; atorvasi pravastatin; clarithromycin; leuproline; paclitaxel; mitobronitol; mitolactol; mopidamol; nogalamycin; olivomycin(s); peplomycin; pirarubicin; prednimustine; puromycin; ranimustine; tubercidin; vinesine; zorubicin; coumetarol; dicoumarol; ethyl biscoumacetate; ethylidine dicoumarol; iloprost; taprostene; tioclomarol; amiprilose; romurtide; sirolimus (rapamycin); tacrolimus; salicyl alcohol; bromosaligenin; ditazol; fepradinol; gentisic acid; glucamethacin; olsalazine; S-adenosylmethionine; azithromycin; salmeterol; budesonide; albuteal; indinavir; fluvastatin; streptozocin; doxorubicin; daunorubicin; plicamycin; idarubicin; pentostatin; metoxantrone; cytarabine; fludarabine phosphate; floxuridine; cladriine; capecitabien; docetaxel; etoposide; topotecan; vinblastine; teniposide, and the like. The therapeutic diol can be selected to be either a saturated or an unsaturated diol.

Suitable naturally occurring and synthetic therapeutic di-acids that can be used to prepare an amide linkage in the PEA polymer compositions of the invention include, for example, bambermycin(s); benazepril; carbenicillin; carzinophillin A; cefixime; cefininox cefpimizole; cefodizime; cefonicid; cefor-anide; cefotetan; ceftazidime; ceftibuten; cephalosporin C; cilastatin; denopterin; edatrexate; enalapril; lisinopril; methotrexate; moxalactam; nifedipine; olsalazine; penicillin N; ramipril; quinacillin; quinapril; temocillin; ticarcillin; Tomudex® (N-[[5-[[(1,4-Dihydro-2-methyl-4-oxo-6-quinazolinyl)methyl]methylamino]-2-thienyl]carbonyl]-L-glutamic acid), and the like. The safety profile of naturally occurring therapeutic di-acids is believed to surpass that of synthetic therapeutic di-acids. The therapeutic di-acid can be either a saturated or an unsaturated di-acid.

The chemical and therapeutic properties of the above described therapeutic diols and di-acids as tumor inhibitors, cytotoxic antimetabolites, antibiotics, and the like, are well known in the art and detailed descriptions thereof can be found, for example, in the 13th Edition of *The Merck Index* (Whitehouse Station, N.J., USA).

The di-aryl sulfonic acid salts of bis(α-amino acid)-diesters of saturated and unsaturated diols can be prepared by admixing α-amino acid, aryl sulfonic acid (e.g., p-toluene sulfonic acid monohydrate) and saturated or unsaturated diol in toluene, heating to reflux temperature, until water evolution is minimal, then cooling. The unsaturated diols include, for example, 2-butene-1,4-diol and 1,18-octadec-9-en-diol.

Saturated di-(p-nitrophenyl) esters of dicarboxylic acid and saturated di-p-toluene sulfonic acid salts of bis(α-amino acid)-alkylene-diesters can be prepared as described in U.S. Pat. No. 6,503,538 B1.

Although the invention bis(α-amino acid)-alkylene-diester containing polymer compositions are poly(ester amides) (PEAs) made by polycondensation of components as described above, in the present invention, the components can include a di-p-toluenesulfonic acid salt of bis(α-amino acid)-1,4:3,6-dianhydrosorbitol diester; a di-p-toluenesulfonic acid salt of bis(α-amino acid)-aliphatic α,ω-diol diester and a di-(p-nitrophenyl) ester of an alkylene dicarboxylic acid. The di-(p-nitrophenyl) esters of dicarboxylic acids are used because the p-nitrophenyl ester is a very good leaving group that can promote the condensation reaction to move to the right of the reaction equation so the polymer product is obtained in high yield. In addition, the di-(p-nitrophenyl) esters are stable throughout workup and can be handled and dried in open atmosphere.

The di-aryl sulfonic acid salts of bis(α-amino acid) dioldiesters of unsaturated diols can be prepared by admixing α-amino acid, p-aryl sulfonic acid (e.g. p-toluene sulfonic acid monohydrate) and saturated or unsaturated diol in toluene, heating to reflux temperature, until water evolution is minimal, then cooling. The unsaturated diols include, for example, 2-butene-1,4-diol and 1,18-octadec-9-en-diol.

A working example of a diamine monomer having structural formula (III), in U.S. Pat. No. 6,503,538 is provided by substituting p-toluene sulfonic acid salt of bis(L-phenylalanine)-2-butene-1,4-diester for (III) in Example 1 of U.S. Pat. No. 6,503,538 or by substituting bis(p-nitrophenyl)fumarate for (V) in Example 1 of U.S. Pat. No. 6,503,538 or by substituting p-toluene sulfonic acid salt of bis(L-phenylalanine)-2-butene-1,4-diester for III in Example 1 of U.S. Pat. No. 6,503,538 and also substituting bis(p-nitrophenyl)fumarate for (V) in Example 1 of U.S. Pat. No. 6,503,538.

In unsaturated PEA, the following hold: Aminoxyl radical e.g., 4-amino TEMPO can be attached using carbonyldiimidazol, or suitable carbodiimide, as a condensing agent. Optionally, bioactive agents, as described herein, can be attached via a double bond functionality, preferably one that does not occur in a residue of a bioactive agent in the polymer backbone. Hydrophilicity, if desired, can be imparted by bonding to poly(ethylene glycol) diacrylate.

The description and methods of synthesis of related PEA polymers are set forth in U.S. Pat. Nos. 5,516,881; 6,476,204; 6,503,538; and in U.S. application Ser. Nos. 10/096,435; 10/101,40 Shirahama H, et al, J. Appl. Polym. Sci. (2001). 80: 340-347; U.S. Ser. Nos. 10/143,572; 10/194,965; 10/362,848, 10/346,848, 10/788,747 and in provisional application 60/576,239, the entire content of each of which is incorporated herein by reference.

The alkylene di-acid-containing PEA polymers described herein have weight average molecular weights ranging from 15,000 to 600,000 Daltons; these polymers and copolymers typically have inherent viscosities at 25° C., determined by standard viscosimetric methods, ranging from 0.3 to 2.0, preferably ranging from 0.4 to 1.7.

The molecular weights and polydispersities herein are determined by gel permeation chromatography (GPC) using polystyrene standards. More particularly, number and weight average molecular weights ($M_n$ and $M_w$) are determined, for example, using a Model 510 gel permeation chromatographer (Water Associates, Inc., Milford, Mass.) equipped with a high-pressure liquid chromatographic pump, a Waters 486 UV detector and a Waters 2410 differential refractive index detector. Solution of 0.1% LiCl in N,N-dimethylacetamide (DMAc) is used as the eluent (1.0 mL/min). The polystyrene (PS) standards, which have a narrow molecular weight distribution, were used for calibration of GPC curves.

The alkylene di-acid-containing PEA polymers described herein can be fabricated in a variety of molecular weights and a variety of relative proportions of the two bis(α-amino acid)-alkylene-diester containing units and optional L-lysine based monomer. The appropriate molecular weight for a particular use is readily determined by one of skill in the art based on the guidelines contained herein and the thermo-mechanical properties disclosed. Thus, e.g., a suitable molecular weight will be on the order of about 15,000 to about 500,000 Daltons, for example about 15,000 to about 300,000, or about 15,000 to about 200,000.

The PEA polymers useful in the invention compositions, biodegradable medical devices and methods of use biodegrade by enzymatic action at the surface. Therefore, the polymers, for example particles thereof, facilitate in vivo release of a bioactive agent dispersed in the polymer at a controlled release rate, which is specific and constant over a prolonged period. Additionally, since PEA polymers break down in vivo via enzymes without production of adverse side products, the polymers in the invention compositions and medical devices, such as those that produce biological α-amino acids upon break down, are substantially non-inflammatory.

Synthesis of the unsaturated poly(ester-amide)s (UPEAs) useful as biodegradable polymers of the structure (I) as described above will now be described. Compounds having the structure (II) can be made in similar fashion to the compound (VII) of U.S. Pat. No. 6,503,538 B1, except that $R^4$ of (III) of U.S. Pat. No. 6,503,538 and/or $R^1$ of (V) of U.S. Pat. No. 6,503,538 is ($C_2$-$C_{20}$) alkenylene as described above. Unsaturated copolymers, co-UPEAs containing different feed ratios of two diamine monomers $R^4$ of (III) of U.S. Pat. No. 6,503,538 will have combinations of above described ($C_2$-$C_{20}$) alkenylene and residue of 1,4:3,6-dianhydrohexitols. And/or $R^1$ in (V) of U.S. Pat. No. 6,508,538 is ($C_2$-$C_{20}$) alkenlylene or combinations of alkenylene and fatty acid residues with various feed ratios. Reaction is carried out, for example, by adding dry triethylamine to a mixture of said (III) and (IV) of U.S. Pat. No. 6,503,538 and said (V) of U.S. Pat. No. 6,503,538 in dry N,N-dimethylacetamide, at room temperature, then increasing the temperature to 80° C. and stirring for 16 hours, then cooling the reaction solution to room temperature, diluting with ethanol, pouring into water, separating polymer, washing separated polymer with water, drying to about 30° C. under reduced pressure and then purifying up to negative test on p-nitrophenyl and p-toluene sulfonic acid. A preferred reactant (IV) of U.S. Pat. No. 6,503,538 is p-toluene sulfonic acid salt of L-lysine benzyl ester, the benzyl ester protecting group is preferably removed from (I) to confer biodegradability, but it should not be removed by hydrogenolysis as in Example 22 of U.S. Pat No. 6,503,538 because hydrogenolysis would saturate the desired double bonds; rather the benzyl ester group should be converted to an acid group by a method that would preserve unsaturation, e.g., by treatment with fluoroacetic acid or gaseous HF. Alternatively, the lysine reactant (IV) of U.S. Pat. No. 6,503,538 can be protected by a protecting group different from benzyl which can be readily removed in the finished product while preserving unsaturation, e.g., the lysine-based reactant can be protected with t-butyl (e.g., the reactant can be t-butyl ester of lysine) and the t-butyl can be converted to the "H" form (free carboxylic acid) while preserving unsaturation by treatment of the product (II) with acid.

In unsaturated compounds having structural formula (I) or (V, the following hold: An amino substituted aminoxyl (N-oxide) radical bearing group e.g., 4-amino TEMPO, can be attached using carbonyldiimidazole, or suitable carbodiimide, as a condensing agent. Bioactive agents, and the like, as described herein, optionally can be attached via the double bond functionality. Hydrophilicity can be imparted by bonding to poly(ethylene glycol) diacrylate.

Polymers contemplated for use in the practice of the invention can be synthesized by a variety of methods well known in the art. For example, tributyltin (IV) catalysts are commonly used to form polyesters such as poly(caprolactone), poly(glycolide), poly(lactide), and the like. However, it is understood that a wide variety of catalysts can be used to form polymers suitable for use in the practice of the invention. Such poly(caprolactones) contemplated for use have an exemplary structural formula (VII) as follows:

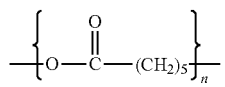

Formula (VII)

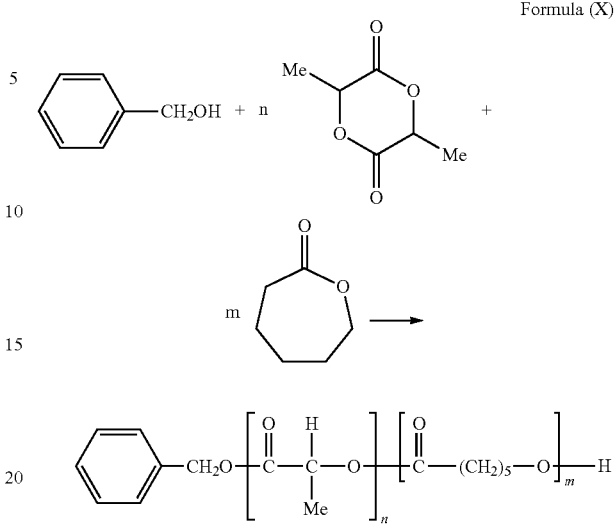

Formula (X)

The hydroxy terminated polymer chains can then be capped with maleic anhydride to form polymer chains having structural formula (XI):

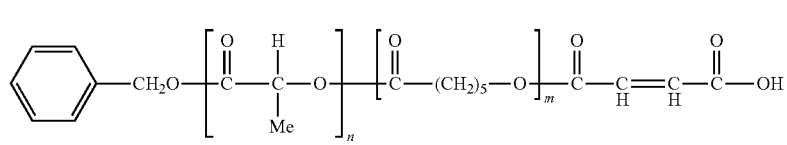

Formula (XI)

Poly(glycolides) contemplated for use have an exemplary structural formula (VIII) as follows:

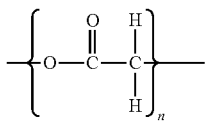

Formula (VIII)

Poly(lactides) contemplated for use have an exemplary structural formula (IX) as follows:

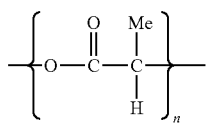

Formula (IX)

An exemplary synthesis of a suitable poly(lactide-co-ε-caprolactone) including an aminoxyl moiety is set forth as follows. The first step involves the copolymerization of lactide and ε-caprolactone in the presence of benzyl alcohol using stannous octoate as the catalyst to form a polymer of structural formula (X):

At this point, 4-amino-2,2,6,6-tetramethylpiperidine-1-oxy can be reacted with the carboxylic end group to covalently attach the aminoxyl moiety to the copolymer via the amide bond which results from the reaction between the 4-amino group and the carboxylic acid end group. Alternatively, the maleic acid capped copolymer can be grafted with polyacrylic acid to provide additional carboxylic acid moieties for subsequent attachment of further aminoxyl groups.

By judicious choice of the content and relative proportions of the three building block units, one skilled in the art can obtain an invention bis (α-amino acid)-containing PEA polymer that is both biodegradable and biocompatible and which possesses a wide range of thermo-mechanical properties.

In certain embodiments, a bioactive agent can be covalently bound to the biodegradable polymers via a wide variety of suitable functional groups. For example, when the biodegradable polymer is a polyester, the carboxylic group chain end can be used to react with a complimentary moiety on the bioactive agent, such as hydroxy, amino, thio, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

In other embodiments, a bioactive agent can be dispersed into the polymer by "loading" onto the polymer without formation of a chemical bond or the bioactive agent can be linked to any free functional group in the polymers, such as an amine, hydroxyl (alcohol), or thiol, and the like, to form a direct linkage. Such a linkage can be formed from suitably functionalized starting materials using synthetic procedures that are known in the art.

For example, a polymer of the present invention can be linked to the bioactive agent via a carboxyl group (e.g., COOH) of the polymer. Specifically, a compound of structures (I and II) can react with an amino functional group of a bioactive agent or a hydroxyl functional group of a bioactive agent to provide a biodegradable, biocompatible polymer having the bioactive agent attached via an amide linkage or ester linkage, respectively. In another embodiment, the carboxyl group of the polymer can be transformed into an acyl halide, acyl anhydride/"mixed" anhydride, or active ester.

Alternatively, the bioactive agent may be attached to the polymer via a linker. Indeed, to improve surface hydrophobicity of the biodegradable polymer, to improve accessibility of the biodegradable polymer towards enzyme activation, and to improve the release profile of the biodegradable polymer, a linker may be utilized to indirectly attach the bioactive agent to the biodegradable polymer. In certain embodiments, the linker compounds include poly(ethylene glycol) having a molecular weight (Mw) of about 44 to about 10,000, preferably 44 to 2000; amino acids, such as serine; polypeptides with repeat units from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is ($C_1$-$C_{24}$) alkyl, ($C_2$-$C_{24}$) alkenyl, ($C_2$-$C_{24}$) alkynyl, ($C_2$-$C_{20}$) alkyloxy, ($C_3$-$C_8$) cycloalkyl, or ($C_6$-$C_{10}$) aryl, and W and Q are each independently —N(R)C(=O)—, —C(=O)N(R)—, —OC(=O)—, —C(=O)O—, —O—, —S—, —S(O)—, —S(O)$_2$—, —S—S—, —N(R)—, —C(=O)—, wherein each R is independently H or ($C_1$-$C_6$) alkyl.

As used herein, the term "alkyl", as applied to the linkers described herein, refers to a straight or branched chain hydrocarbon group including methyl, ethyl, n-propyl, isopropyl, n-butyl, isobutyl, tert-butyl, n-hexyl, and the like.

As used herein, "alkenyl", as applied to the linkers described herein, refers to straight or branched chain hydrocarbon groups having one or more carbon-carbon double bonds.

As used herein, "alkynyl", as applied to the linkers described herein, refers to straight or branched chain hydrocarbon groups having at least one carbon-carbon triple bond.

As used herein, "aryl", as applied to the linkers described herein, refers to aromatic groups having in the range of 6 up to 14 carbon atoms.

In certain embodiments, the linker may be a polypeptide having from about 2 up to about 25 amino acids. Suitable peptides contemplated for use include poly-L-lysine, poly-L-glutamic acid, poly-L-aspartic acid, poly-L-histidine, poly-L-ornithine, poly-L-threonine, poly-L-tyrosine, poly-L-leucine, poly-L-lysine-L-phenylalanine, poly-L-arginine, poly-L-lysine-L-tyrosine, and the like.

The linker can be attached first to the polymer or to the bioactive agent. During synthesis of polymers having bioactive agents indirectly attached via a linker, the linker can be either in unprotected form or protected from, using a variety of protecting groups well known to those skilled in the art.

In the case of a protected linker, the unprotected end of the linker can first be attached to the polymer or the bioactive agent. The protecting group can then be de-protected using Pd/$H_2$ hydrogenolysis for saturated polymers, mild acid or base hydrolysis for unsaturated polymers, or any other common de-protection method that is known in the art. The de-protected linker can then be attached to the bioactive agent. Poly(ethylene glycol) can also be employed as the linker between polymer and bioactive agent.

The following illustrates synthesis of a polymer composition according to the invention (wherein the bioactive agent is an aminoxyl). A polyester can be reacted with an amino substituted aminoxyl (N-oxide) radical bearing group, e.g., 4-amino-2,2,6,6-tetramethylpiperidine-1-oxy, in the presence of N,N'-carbonyldiimidazole or suitable carbodiimide to replace the hydroxyl moiety in the carboxyl group at the chain end of the polyester with an amino substituted aminoxyl (N-oxide) radical bearing group, so that the amino moiety covalently bonds to the carbon of the carbonyl residue of the carboxyl group to form an amide bond. The N,N'-carbonyldiimidazole or suitable carbodiimide converts the hydroxyl moiety in the carboxyl group at the chain end of the polyester into an intermediate activated moiety which will react with the aminoxyl, e.g., 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyldiimidazole to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or hexafluoroisopropanol at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, methylene chloride and chloroform at room temperature to 50° C. suitably dissolve the polyester.

The reaction is typically carried out to substantial completion in 30 minutes to 5 hours. When a polyglycolic acid or a poly(glycolide-L-lactide) from a glycol-rich monomer mixture constitutes the polyester, 2 to 3 hours of reaction time is preferred. When a poly-L-lactic acid is the polyester, the reaction is readily carried out to substantial completion at room temperature for one hour. The reaction is preferably carried out under an inert atmosphere with dry nitrogen purging so as to drive the reaction towards completion.

The product may be precipitated from the reaction mixture by adding cold non-solvent for the product. For example, aminoxyl-containing polyglycolic acid and aminoxyl-containing poly(glycolide-L-lactide) formed from glycolic acid-rich monomer mixture are readily precipitated from hot dimethylsulfoxide by adding cold methanol or cold acetone/methanol mixture and then recovered, e.g., by filtering. When the product is not readily precipitated by adding cold non-solvent for the product, the product and solvent may be separated by using vacuum techniques. For example, aminoxyl-containing poly-L-lactic acid is advantageously separated from solvent in this way. The recovered product is readily further purified by washing away water and by-products (e.g. urea) with a solvent which does not dissolve the product, e.g., methanol in the case of the modified polyglycolic acid, poly-lactic acid and poly(glycolide-L-lactide) products herein. Residual solvent from such washing may be removed using vacuum drying.

While the optional bioactive agent(s) can be dispersed within the polymer matrix without chemical linkage to the polymer carrier, it is also contemplated that one or more bioactive agents or covering molecules can be covalently bound to the biodegradable polymers via a wide variety of suitable functional groups. For example, a free carboxyl group can be used to react with a complimentary moiety on a bioactive agent or covering molecule, such as a hydroxy, amino, or thio group, and the like. A wide variety of suitable reagents and reaction conditions are disclosed, e.g., in *March's Advanced Organic Chemistry, Reactions, Mechanisms, and Structure*, Fifth Edition, (2001); and *Comprehensive Organic Transformations*, Second Edition, Larock (1999).

In other embodiments, one or more bioactive agent can be linked to any of the polymers of structures (I, IV or V) through an amide, ester, ether, amino, ketone, thioether, sulfinyl, sulfonyl, or disulfide linkage. Such a linkage can be formed from suitably functionalized starting materials using synthetic procedures that are known in the art.

For example, in one embodiment a polymer can be linked to a bioactive agent or adjuvant via a free carboxyl group (e.g., COOH) of the polymer. Specifically, a compound of structures (I) and (II) can react with an amino functional group or a hydroxyl functional group of a bioactive agent to provide a biodegradable polymer having the bioactive agent attached via an amide linkage or ester linkage, respectively. In another embodiment, the carboxyl group of the polymer can be benzylated or transformed into an acyl halide, acyl anhydride/"mixed" anhydride, or active ester. In other embodiments, the free —$NH_2$ ends of the polymer molecule can be acylated to assure that the bioactive agent will attach only via a carboxyl group of the polymer and not to the free ends of the polymer.

The invention alkylene di-acid-containing PEA polymer compositions can be formulated into particles to provide a variety of properties. The particles can have a variety of sizes and structures suitable to meet differing therapeutic goals and routes of administration using methods described in full in co-pending U.S. provisional applications 60/654,715, filed Feb. 17, 2005; 60/684,670, filed May 25, 2005; 60/737,401, filed on Nov. 14, 2005.

Water soluble covering molecule(s), such as poly(ethylene glycol) (PEG); phosphatidylcholine (PC); glycosaminoglycans including heparin; polysaccharides including chitosan, alginates and polysialic acid; poly(ionizable or polar amino acids) including polyserine, polyglutamic acid, polyaspartic acid, polylysine and polyarginine; as described herein, and targeting molecules, such as antibodies, antigens and ligands, are bioactive agents that can also be conjugated to the polymer on the exterior of particles or medical devices formed from the invention polymer compositions after production to block active sites thereon not occupied by a bioactive agent or to target delivery of the particles to a specific body site as is known in the art. The molecular weights of PEG molecules on a single particle can be substantially any molecular weight in the range from about 200 to about 200,000, so that the molecular weights of the various PEG molecules attached to the particle can be varied.

Alternatively, a bioactive agent or covering molecule can be attached to the polymer via a linker molecule. Indeed, to improve surface hydrophobicity of the biodegradable polymer, to improve accessibility of the biodegradable polymer towards enzyme activation, and to improve the release profile of the bioactive agents from the biodegradable polymer, a linker may be utilized to indirectly attach a bioactive agent to the biodegradable polymer. In certain embodiments, the linker compounds include poly(ethylene glycol) having a molecular weight (Mw) of about 44 to about 10,000, preferably 44 to 2000; amino acids, such as serine; polypeptides with repeat number from 1 to 100; and any other suitable low molecular weight polymers. The linker typically separates the bioactive agent from the polymer by about 5 angstroms up to about 200 angstroms.

In still further embodiments, the linker is a divalent radical of formula W-A-Q, wherein A is ($C_1$-$C_{24}$) alkyl, ($C_2$-$C_{24}$) alkenyl, ($C_2$-$C_{24}$) alkynyl, ($C_2$-$C_{20}$) alkyloxy, ($C_3$-$C_8$) cycloalkyl, or ($C_6$-$C_{10}$) aryl, and W and Q are each independently —N(R)C(=O)—, —C(=O)N(R)—, —OC(=O)—, —C(=O)O—, —O—, —S—, —S(O), —S(O)$_2$—, —S—S—, —N(R)—, —C(=O)—, wherein each R is independently H or ($C_1$-$C_6$) alkyl.

As used to describe the above linkers, the term "alkyl" refers to a straight or branched chain hydrocarbon group including methyl, ethyl, n-propyl, isopropyl, n-butyl, isobutyl, tert-butyl, n-hexyl, and the like.

As used to describe the above linkers, "alkenyl" refers to straight or branched chain hydrocarbyl groups having one or more carbon-carbon double bonds.

As used to describe the above linkers, "alkynyl" refers to straight or branched chain hydrocarbyl groups having at least one carbon-carbon triple bond.

As used to describe the above linkers, "aryl" refers to aromatic groups having in the range of 6 up to 14 carbon atoms.

In certain embodiments, the linker may be a polypeptide having from about 2 up to about 25 amino acids. Suitable peptides contemplated for use include poly-L-glycine, poly-L-lysine, poly-L-glutamic acid, poly-L-aspartic acid, poly-L-histidine, poly-L-ornithine, poly-L-serine, poly-L-threonine, poly-L-tyrosine, poly-L-leucine, poly-L-lysine-L-phenylalanine, poly-L-arginine, poly-L-lysine-L-tyrosine, and the like.

In one embodiment, a bioactive agent can covalently crosslink the polymer, i.e. the bioactive agent is bound to more than one polymer molecule, to form an intermolecular bridge. This covalent crosslinking can be done with or without a linker containing a bioactive agent.

A bioactive agent molecule can also be incorporated into an intramolecular bridge by covalent attachment between two sites on the same polymer molecule.

A linear polymer polypeptide conjugate is made by protecting the potential nucleophiles on the polypeptide backbone and leaving only one reactive group to be bound to the polymer or polymer linker construct. Deprotection is performed according to methods well known in the art for deprotection of peptides (Boc and Fmoc chemistry for example).

In one embodiment of the present invention, a bioactive agent is a polypeptide presented as a retro-inverso or partial retro-inverso peptide.

In other embodiments, a bioactive agent may be mixed with a photocrosslinkable version of the polymer in a matrix, and, after crosslinking, the material is dispersed (ground) to form particles having an average diameter in the range from about 0.1 to about 10µm.

The linker can be attached first to the polymer or to the bioactive agent or covering molecule. During synthesis, the linker can be either in unprotected form or protected from, using a variety of protecting groups well known to those skilled in the art. In the case of a protected linker, the unprotected end of the linker can first be attached to the polymer or the bioactive agent or covering molecule. The protecting group can then be de-protected using Pd/$H_2$ hydrogenation for saturated polymer backbones, mild acid or base hydrolysis for unsaturated polymers, or any other common de-protection method that is known in the art. The de-protected linker can then be attached to the bioactive agent or covering molecule, or to the polymer An exemplary conjugate synthesis performed on a biodegradable polymer according to the invention (wherein the molecule to be attached to the polymer is an amino substituted aminoxyl N-oxide radical) is set forth as follows. A biodegradable polymer herein can be reacted with an aminoxyl radical containing compound, e.g., 4-amino-2,2,6,6-tetramethylpiperidine-1-oxy, in the presence of N,N'-carbonyl diimidazole or suitable carbodiimide, to replace the hydroxyl moiety in the carboxyl group, either on the pendant carboxylic acids of the PEAs or UPEAs, or at the chain end of a polyester as described, with an amide linkage to the aminoxyl (N-oxide) radical containing group. The amino moiety covalently bonds to the carbon of the carbonyl residue such that an amide bond is formed. The N,N'-carbonyldiimidazole or suitable carbodiimide converts the hydroxyl moiety in the carboxyl group at the chain end of the polyester into an intermediate activated moiety which will react with the amino group of the aminoxyl (N oxide) radical compound, e.g., the amine at position 4 of 4-amino-2,2,6,6-tetramethylpiperidine-1-oxy. The aminoxyl reactant is typically used in a mole ratio of reactant to polyester ranging from 1:1 to 100:1. The mole ratio of N,N'-carbonyldiimidazole or carbodiimide to aminoxyl is preferably about 1:1.

A typical reaction is as follows. A polyester is dissolved in a reaction solvent and reaction is readily carried out at the temperature utilized for the dissolving. The reaction solvent may be any in which the polyester will dissolve; this information is normally available from the manufacturer of the polyester. When the polyester is a polyglycolic acid or a poly(glycolide-L-lactide) (having a monomer mole ratio of glycolic acid to L-lactic acid greater than 50:50), highly refined (99.9+% pure) dimethyl sulfoxide at 115° C. to 130° C. or DMSO at room temperature suitably dissolves the polyester. When the polyester is a poly-L-lactic acid, a poly-DL-lactic acid or a poly(glycolide-L-lactide) (having a monomer mole ratio of glycolic acid to L-lactic acid 50:50 or less than 50:50), tetrahydrofuran, dichloromethane (DCM) and chloroform at room temperature to 40~50° C. suitably dissolve the polyester.

Polymer—Bioactive Agent Linkage

In one embodiment, the polymers used to make the invention alkylene di-acid-containing PEA polymer compositions as described herein have one or more bioactive agent directly linked to the polymer. The residues of the polymer can be linked to the residues of the one or more bioactive agents. For example, one residue of the polymer can be directly linked to one residue of a bioactive agent. The polymer and the bioactive agent can each have one open valence. Alternatively, more than one bioactive agent, multiple bioactive agents, or a mixture of bioactive agents having different therapeutic or palliative activity can be directly linked to the polymer. However, since the residue of each bioactive agent can be linked to a corresponding residue of the polymer, the number of residues of the one or more bioactive agents can correspond to the number of open valences on the residue of the polymer.

As used herein, a "residue of a polymer" refers to a radical of a polymer having one or more open valences. Any synthetically feasible atom, atoms, or functional group of the polymer (e.g., on the polymer backbone or pendant group) is substantially retained when the radical is attached to a residue of a bioactive agent. Additionally, any synthetically feasible functional group (e.g., carboxyl) can be created on the polymer (e.g., on the polymer backbone as a pendant group or as chain termini) to provide the open valence, provided bioactivity of the backbone bioactive agent is substantially retained when the radical is attached to a residue of a bioactive agent. Based on the linkage that is desired, those skilled in the art can select suitably functionalized starting materials that can be used to derivatize the PEA polymers used in the present invention using procedures that are known in the art.

As used herein, a "residue of a compound of structural formula (*)" refers to a radical of a compound of polymer formulas (I, IV or V) as described herein having one or more open valences. Any synthetically feasible atom, atoms, or functional group of the compound (e.g., on the polymer backbone or pendant group) can be removed to provide the open valence, provided bioactivity of the backbone bioactive agent is substantially retained when the radical is attached. Additionally, any synthetically feasible functional group (e.g., carboxyl) can be created on the compound of formulas (I, IV or V) (e.g., on the polymer backbone or pendant group) to provide the open valence, provided bioactivity of the backbone bioactive agent is substantially retained when the radical is attached to a residue of a bioactive agent. Based on the linkage that is desired, those skilled in the art can select suitably functionalized starting materials that can be used to derivatize the compound of formulas (I, IV or V) using procedures that are known in the art.

For example, the residue of a bioactive agent can be linked to the residue of a compound of structural formulas (I and II) through an amide (e.g., —N(R)C(=O)— or C(=O)N(R)—), ester (e.g., —OC(=O)— or —C(=O)O—, ether (e.g., —O—), amino (e.g., —N(R)—), ketone (e.g., —C(=O)—), thioether (e.g., —S—), sulfinyl (e.g., —S(O)—), sulfonyl (e.g., —S(O)$_2$—), disulfide (e.g., —S—S—), or a direct (e.g., C—C bond) linkage, wherein each R is independently H or (C$_1$-C$_6$) alkyl. Such a linkage can be formed from suitably functionalized starting materials using synthetic procedures that are known in the art. Based on the linkage that is desired, those skilled in the art can select suitably functional starting material to derivatize any residue of a compound of structural formulas (I, IV or V) and thereby conjugate a given residue of a bioactive agent using procedures that are known in the art. The residue of the optional bioactive agent can be linked to any synthetically feasible position on the residue of a compound of structural formulas (I, IV or V). Additionally, the invention also provides compounds having more than one residue of a bioactive agent directly linked to a compound of structural formulas (I, IV or V).

The number of bioactive agents that can be linked to the polymer molecule can typically depend upon the molecular weight of the polymer. For example, for a compound of structural formula (I), wherein n is about 5 to about 150, preferably about 5 to about 70, up to about 300 bioactive agent molecules (i.e., residues thereof) can be directly linked to the polymer (i.e., residue thereof) by reacting the bioactive agent with terminal groups of the polymer. On the other hand, for a compound of structural formula (V) up to an additional 150 bioactive agents can be linked to the polymer by reacting the bioactive agent with the pendant group on the lysine-containing unit. In unsaturated polymers, additional bioactive agents can also be reacted with double (or triple) bonds in the polymer.

The invention alkylene di-acid containing PEA composition, either in the form of particles or medical devices, or not, can be covalently attached directly to the bioactive agent, rather than being dispersed or "loaded" into the polymer without chemical attachment, using any of several methods well known in the art and as described hereinbelow. The amount of bioactive agent is generally approximately 0.1% to about 60% (w/w) bioactive agent to polymer composition, more preferably about 1% to about 25% (w/w) bioactive agent, and even more preferably about 2% to about 20% (w/w) bioactive agent. The percentage of bioactive agent will depend on the desired dose and the condition being treated, as discussed in more detail below.

In addition to serving as a stand-alone delivery system for bioactive agents when directly administered in vivo in the form of implantable particles, and the like, the invention alkylene di-acid-containing polymer compositions can be used in the fabrication of various types of surgical devices. In this embodiment, the invention polymer composition used in fabrication of the medical device is effective for controlled delivery to surrounding tissue of any bioactive agents dispersed in the polymer in the invention polymer composition, for example, covalently attached to the surface thereof.

In one embodiment, the invention alkylene di-acid-containing PEA polymer composition has sufficient stiffness to be fabricated in the form of a biodegradable, biocompatible surgical device, including but not limited to internal fixation devices, such as surgical suture, surgical screws, implantable plates, and implantable rods, or as vascular stents and dialysis shunts. Any method known in the art for fabrication of biodegradable polymer medical devices, such as extrusion, injection molding, casting, or solution processing (dry and wet spinning), and the like, can be used for this purpose. Such biodegradable, biocompatible medical devices slowly biodegrade, for example over a period of from about 7 to about 14 days to a few years, for example about one year, three years or six years, depending on selection of polymer building blocks and device thickness, to create substantially biocompatible breakdown products.

In another embodiment the invention provides methods for delivering a bioactive agent to a subject in need thereof comprising implanting an invention composition at an interior body site so that the composition slowly biodegrades, for example completely. Any dispersed bioactive agent, as described herein dispersed in the polymer will be slowly released during biodegradation to tissue surrounding a site of implantation, for example to promote healing and alleviate pain therein. No additional surgery is required to remove the implanted surgical device due to its biodegradation properties.

In another embodiment, the invention alkylene di-acid-containing PEA polymer composition can be fabricated in the form of a biodegradable, biocompatible pad, sheet or wrap of any desired surface area. For example, the polymer can be woven or formed as a thin sheet of randomly oriented fibers by electrospinning to produce nanofibers of the polymer. Such pads, sheets and wraps can be used in a number of types of wound dressings for treatment of a variety of conditions, for example by promoting endogenous healing processes at a wound site. The polymer compositions in the wound dressing biodegrade over time, releasing the bioactive agent to be absorbed into a wound site where it acts intracellularly, either within the cytosol, the nucleus, or both of a target cell, or the bioactive agent can bind to a cell surface receptor molecule to elicit a cellular response without entering the cell. Alternatively, the bioactive agent can be released from the surgical device, such as a vascular stent, having at least one surface partially coated with the invention composition to promote endogenous healing processes at the wound site by contact with the surroundings into which the medical device is implanted. A detailed description of wound dressings, wound healing implants and surgical device coatings made using PEA polymers is found in co-pending U.S. patent application Ser. No. 11/128,903, filed May 12, 2005.

Bioactive agents contemplated for dispersion within the polymers used in the invention alkylene di-acid-containing PEA polymer compositions include anti-proliferants, rapamycin and any of its analogs or derivatives, paclitaxel or any of its taxene analogs or derivatives, everolimus, sirolimus, tacrolimus, or any of its-limus named family of drugs, and statins such as simvastatin, atorvastatin, fluvastatin, pravastatin, lovastatin, rosuvastatin, geldanamycins, such as 17AAG (17-allylamino-17-demethoxygeldanamycin); Epothilone D and other epothilones, 17-dimethylaminoethylamino-17-demethoxy-geldanamycin and other polyketide inhibitors of heat shock protein 90 (Hsp90), cilostazol, and the like.

Suitable bioactive agents for dispersion in the invention alkylene di-acid-containing PEA polymer compositions and particles made therefrom also can be selected from those that promote endogenous production of a therapeutic natural wound healing agent, such as nitric oxide, which is endogenously produced by endothelial cells. Alternatively the bioactive agents released from the polymers during degradation may be directly active in promoting natural wound healing processes by endothelial cells. These bioactive agents can be any agent that donates, transfers, or releases nitric oxide, elevates endogenous levels of nitric oxide, stimulates endogenous synthesis of nitric oxide, or serves as a substrate for nitric oxide synthase or that inhibits proliferation of smooth muscle cells. Such agents include, for example, aminoxyls, furoxans, nitrosothiols, nitrates and anthocyanins; nucleosides such as adenosine and nucleotides such as adenosine diphosphate (ADP) and adenosine triphosphate (ATP);neurotransmitter/neuromodulators such as acetylcholine and 5-hydroxytryptamine (serotonin/5-HT); histamine and catecholamines such as adrenalin and noradrenalin; lipid molecules such as sphingosine-1-phosphate and lysophosphatidic acid; amino acids such as arginine and lysine; peptides such as the bradykinins, substance P and calcium gene-related peptide (CGRP), and proteins such as insulin, vascular endothelial growth factor (VEGF), and thrombin.

A variety of bioactive agents, coating molecules and ligands for bioactive agents can be attached, for example covalently, to the surface of the polymer particles. Bioactive agents, such as targeting antibodies, polypeptides (e.g., antigens) and drugs can be covalently conjugated to the surface of the polymer particles. In addition, coating molecules, such as polyethylene glycol (PEG) as a ligand for attachment of antibodies or polypeptides or phosphatidylcholine (PC) as a means of blocking attachment sites on the surface of the particles, can be surface-conjugated to the particles to prevent the particles from sticking to non-target biological molecules and surfaces in a subject to which the particles are administered.

For example, small proteinaceous motifs, such as the B domain of bacterial Protein A and the functionally equivalent region of Protein G are known to bind to, and thereby capture, antibody molecules by the Fc region. Such proteinaceous motifs can be attached as bioactive agents to the invention polymers and compositions, especially to the surface of the polymer particles described herein. Such molecules will act, for example, as ligands to attach antibodies for use as targeting ligands or to capture antibodies to hold precursor cells or capture cells out of the blood stream. Therefore, the antibody types that can be attached to polymer coatings using a Protein A or Protein G functional region are those that contain an Fc region. The capture antibodies will in turn bind to and hold precursor cells, such as progenitor cells, near the polymer surface while the precursor cells, which are preferably bathed in a growth medium within the polymer, secrete various factors and interact with other cells of the subject. In addition, one or more bioactive agents dispersed in the polymer particles, such as the bradykinins, may activate the precursor cells.

In addition, bioactive agents for attaching precursor cells or for capturing progenitor endothelial cells (PECs) from a blood stream in a subject to which the polymer compositions are administered are monoclonal antibodies directed against a known precursor cell surface marker. For example, complementary determinants (CDs) that have been reported to decorate the surface of endothelial cells include CD31, CD34, CD102, CD105, CD106, CD109, CDw130, CD141, CD142, CD143, CD144, CDw145, CD146, CD147, and CD166. These cell surface markers can be of varying specificity and the degree of specificity for a particular cell/developmental type/stage is in many cases not fully characterized. In addition, these cell marker molecules against which antibodies have been raised will overlap (in terms of antibody recognition) especially with CDs on cells of the same lineage: monocytes in the case of endothelial cells. Circulating endothelial progenitor cells are some way along the developmental pathway from (bone marrow) monocytes to mature endothelial cells. CDs 106, 142 and 144 have been reported to mark mature endothelial cells with some specificity. CD34 is presently known to be specific for progenitor endothelial cells and therefore is currently preferred for capturing progenitor endothelial cells out of blood in the site into which the polymer particles are implanted for local delivery of the active agents. Examples of such antibodies include single-chain antibodies, chimeric antibodies, monoclonal antibodies, polyclonal antibodies, antibody fragments, Fab fragments, IgA, IgG, IgM, IgD, IgE and humanized antibodies, and active fragments thereof.

The following bioactive agents and small molecule drugs will be particularly effective for dispersion within the invention alkylene di-acid-containing PEA polymer compositions. The bioactive agents that are dispersed in the invention alkylene di-acid-containing polymer compositions and medical devices made thereof will be selected for their suitable therapeutic or palliative effect in treatment of a wound or disease of interest, or symptoms thereof, or in experiments designed for in vitro testing of such effects in cells or tissue culture, or in vivo.

In one embodiment, the suitable bioactive agents are not limited to, but include, various classes of compounds that facilitate or contribute to wound healing when presented in a time-release fashion. Such bioactive agents include wound-healing cells, including certain precursor cells, which can be protected and delivered by the biodegradable polymer in the invention compositions. Such wound healing cells include, for example, pericytes and endothelial cells, as well as inflammatory healing cells. To recruit such cells to the site of a polymer depot in vivo, the invention alkylene di-acid-containing PEA polymer compositions and particles thereof used in the invention and methods of use can include ligands for such cells, such as antibodies and smaller molecule ligands, that specifically bind to "cellular adhesion molecules" (CAMs). Exemplary ligands for wound healing cells include those that specifically bind to Intercellular adhesion molecules (ICAMs), such as ICAM-1 (CD54 antigen); ICAM-2 (CD102 antigen); ICAM-3 (CD50 antigen); ICAM-4 (CD242 antigen); and ICAM-5; Vascular cell adhesion molecules (VCAMs), such as VCAM-1 (CD106 antigen); Neural cell adhesion molecules (NCAMs), such as NCAM-1 (CD56 antigen); or NCAM-2; Platelet endothelial cell adhesion molecules PECAMs, such as PECAM-1 (CD31 antigen); Leukocyte-endothelial cell adhesion molecules (ELAMs), such as LECAM-1; or LECAM-2 (CD62E antigen), and the like.

In another aspect, the suitable bioactive agents include extra cellular matrix proteins, macromolecules that can be dispersed into the polymer particles used in the invention alkylene di-acid-containing PEA polymer compositions, e.g., attached either covalently or non-covalently. Examples of useful extra-cellular matrix proteins include, for example, glycosaminoglycans, usually linked to proteins (proteoglycans), and fibrous proteins (e.g., collagen; elastin; fibronectins and laminin). Bio-mimics of extra-cellular proteins can also be used. These are usually non-human, but biocompatible, glycoproteins, such as alginates and chitin derivatives. Wound healing peptides that are specific fragments of such extra-cellular matrix proteins and/or their bio-mimics can also be used.

Proteinaceous growth factors are another category of bioactive agents suitable for dispersion in the invention alkylene di-acid-containing PEA polymer compositions and methods of use described herein. Such bioactive agents are effective in promoting wound healing and other disease states as is known in the art, for example, Platelet Derived Growth Factor-BB (PDGF-BB), Tumor Necrosis Factor-alpha (TNF-alpha), Epidermal Growth Factor (EGF), Keratinocyte Growth Factor (KGF), Thymosin B4; and, various angiogenic factors such as vascular Endothelial Growth Factors (VEGFs), Fibroblast Growth Factors (FGFs), Tumor Necrosis Factor-beta (TNF -beta), and Insulin-like Growth Factor-1 (IGF-1). Many of these proteinaceous growth factors are available commercially or can be produced recombinantly using techniques well known in the art.

Alternatively, expression systems comprising vectors, particularly adenovirus vectors, incorporating genes encoding a variety of biomolecules can be dispersed in the invention alkylene di-acid-containing polymer compositions and particles thereof for timed release delivery. Methods of preparing such expression systems and vectors are well known in the art. For example, proteinaceous growth factors can be dispersed into the invention bioactive compositions for administration of the growth factors either to a desired body site for local delivery, by selection of particles sized to form a polymer depot, or systemically, by selection of particles of a size that will enter the circulation. Growth factors, such as VEGFs, PDGFs, FGF, NGF, and evolutionary and functionally related biologics, and angiogenic enzymes, such as thrombin, may also be used as bioactive agents in the invention.

Small molecule drugs are yet another category of bioactive agents suitable for dispersion in the invention alkylene di-acid-containing PEA polymer compositions and methods of use described herein. Such drugs include, for example, antimicrobials and anti-inflammatory agents as well as certain healing promoters, such as, for example, vitamin A and synthetic inhibitors of lipid peroxidation.

A variety of antibiotics can be dispersed as bioactive agents in the invention alkylene di-acid-containing PEA polymer compositions to indirectly promote natural healing processes by preventing or controlling infection. Suitable antibiotics include many classes, such as aminoglycoside antibiotics or quinolones or beta-lactams, such as cefalosporins, e.g., ciprofloxacin, gentamycin, tobramycin, erythromycin, vancomycin, oxacillin, cloxacillin, methicillin, lincomycin, ampicillin, and colistin. Suitable antibiotics have been described in the literature.

Suitable antimicrobials include, for example, Adriamycin PFS/RDF® (Pharmacia and Upjohn), Blenoxane® (Bristol-Myers Squibb Oncology/Immunology), Cerubidine® (Bedford), Cosmegen® (Merck), DaunoXome® (NeXstar), Doxil® (Sequus), Doxorubicin Hydrochloride® (Astra), Idamycin® PFS (Pharmacia and Upjohn), Mithracin® (Bayer), Mitamycin® (Bristol-Myers Squibb Oncology/Immunology), Nipen® (SuperGen), Novantrone® (Immunex) and Rubex® (Bristol-Myers Squibb Oncology/Immunology). In one embodiment, the peptide can be a glycopeptide. "Glycopeptide" refers to oligopeptide (e.g. heptapeptide) antibiotics, characterized by a multi-ring peptide core optionally substituted with saccharide groups, such as vancomycin.

Examples of glycopeptides included in this category of antimicrobials may be found in "Glycopeptides Classification, Occurrence, and Discovery," by Raymond C. Rao and Louise W. Crandall, ("Bioactive agents and the Pharmaceutical Sciences" Volume 63, edited by Ramakrishnan Nagarajan, published by Marcal Dekker, Inc.). Additional examples of glycopeptides are disclosed in U.S. Pat. Nos. 4,639,433; 4,643,987; 4,497,802; 4,698,327, 5,591,714; 5,840,684; and 5,843,889; in EP 0 802 199; EP 0 801 075; EP 0 667 353; WO 97/28812; WO 97/38702; WO 98/52589; WO 98/52592; and in *J. Amer. Chem. Soc.* (1996) 118: 13107-13108; *J. Amer. Chem. Soc.* (1997) 119:12041-12047; and *J. Amer. Chem. Soc.* (1994) 116:4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimyein, Chloroorientiein, Chloropolysporin, Decaplanin, -demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UD-69542, UK-72051, Vancomycin, and the like. The term "glycopeptide" or "glycopeptide antibiotic" as used herein is also intended to include the general class of glycopeptides disclosed above on which the sugar moiety is absent, i.e. the aglycone series of glycopeptides. For example, removal of the disaccharide moiety appended to the phenol on vancomycin by mild hydrolysis gives vancomycin aglycone. Also included within the scope of the term "glycopeptide antibiotics" are synthetic derivatives of the general class of glycopeptides disclosed above, including alkylated and acylated derivatives. Additionally, within the scope of this term are glycopeptides that have been further appended with additional saccharide residues, especially aminoglycosides, in a manner similar to vancosamine.

The term "lipidated glycopeptide" refers specifically to those glycopeptide antibiotics that have been synthetically modified to contain a lipid substituent. As used herein, the term "lipid substituent" refers to any substituent contains 5 or more carbon atoms, preferably, 10 to 40 carbon atoms. The lipid substituent may optionally contain from 1 to 6 heteroatoms selected from halo, oxygen, nitrogen, sulfur, and phosphorous. Lipidated glycopeptide antibiotics are well known in the art. See, for example, in U.S. Pat. Nos. 5,840,684, 5,843,889, 5,916,873, 5,919,756, 5,952,310, 5,977,062, 5,977,063, EP 667, 353, WO 98/52589, WO 99/56760, WO 00/04044, WO 00/39156, the disclosures of which are incorporated herein by reference in their entirety.

Anti-inflammatory bioactive agents are also useful for dispersion in used in invention alkylene di-acid-containing PEA polymer compositions and methods. Depending on the body site and disease to be treated, such anti-inflammatory bioactive agents include, e.g. analgesics (e.g., NSAIDS and salicyclates), steroids, antirheumatic agents, gastrointestinal agents, gout preparations, hormones (glucocorticoids), nasal preparations, ophthalmic preparations, otic preparations (e.g., antibiotic and steroid combinations), respiratory agents, and skin & mucous membrane agents. See, *Physician 's Desk Reference*, 2005 Edition. Specifically, the anti-inflammatory agent can include dexamethasone, which is chemically designated as (11I,16I)-9-fluro-11,17,21-trihydroxy-16-methyl-pregna-1,4-diene-3,20-dione. Alternatively, the anti-inflammatory bioactive agent can be or include sirolimus (rapamycin), which is a triene macrolide antibiotic isolated from *Streptomyces hygroscopicus*.

The polypeptide bioactive agents included in the invention compositions and methods can also include "peptide mimetics." Such peptide analogs, referred to herein as "peptide mimetics" or "peptidomimetics," are commonly used in the pharmaceutical industry with properties analogous to those of the template peptide (Fauchere, J. (1986) *Adv. Bioactive agent Res.*, 15:29; Veber and Freidinger (1985) *TINS*, p. 392; and Evans et al. (1987) *J. Med. Chem.*, 30:1229) and are usually developed with the aid of computerized molecular modeling. Generally, peptidomimetics are structurally similar to a paradigm polypeptide (i.e., a polypeptide that has a biochemical property or pharmacological activity), but have one or more peptide linkages optionally replaced by a linkage selected from the group consisting of: —$CH_2NH$—, —$CH_2S$—, $CH_2$—$CH_2$—, —CH=CH— (cis and trans), —$COCH_2$—, —$CH(OH)CH_2$—, and —$CH_2SO$—, by methods known in the art and further described in the following references: Spatola, A. F. in *Chemistry and Biochemistry of Amino Acids, Peptides, and Proteins*, B. Weinstein, eds., Marcel Dekker, New York, p. 267 (1983); Spatola, A. F., *Vega Data* (March 1983), Vol. 1, Issue 3, "Peptide Backbone Modifications" (general review); Morley, J. S., *Trends. Pharm. Sci.*, (1980) pp. 463-468 (general review); Hudson, D. et al., *Int. J. Pept. Prot. Res.*, (1979)14:177-185 (—$CH_2NH$—, $CH_2CH_2$—); Spatola, A. F. et al., *Life Sci.*, (1986) 38:1243-1249 (—$CH_2$—S—); Harm, M. M., *J. Chem. Soc. Perkin Trans I* (1982) 307-314 (—CH=CH—, cis and trans); Almquist, R. G. et al., *J. Med. Chem.*, (1980) 23:2533 (—$COCH_2$—); Jennings-White, C. et al., *Tetrahedron Lett.*, (1982) 23:2533 (—$COCH_2$—); Szelke, M. et al., European Appln., EP 45665 (1982) CA: 97:39405 (1982) (—CH(OH) $CH_2$—); Holladay, M. W. et al., *Tetrahedron Lett.*, (1983) 24:4401-4404 (—C(OH)$CH_2$—); and Hruby, V. J., *Life Sci.*, (1982) 31:189-199 (—$CH_2$—S—). Such peptide mimetics may have significant advantages over natural polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others.

Additionally, substitution of one or more amino acids within a peptide (e.g., with a D-lysine in place of L-lysine) may be used to generate more stable peptides and peptides resistant to endogenous peptidases. Alternatively, the synthetic polypeptides covalently bound to the biodegradable polymer, can also be prepared from D-amino acids, referred to as inverso peptides. When a peptide is assembled in the opposite direction of the native peptide sequence, it is referred to as a retro peptide. In general, polypeptides prepared from D-amino acids are very stable to enzymatic hydrolysis. Many cases have been reported of preserved biological activities for retro-inverso or partial retro-inverso polypeptides (U.S. Pat. No. 6,261,569 B 1 and references therein; B. Fromme et al, *Endocrinology* (2003)144:3262-3269.

Any suitable and effective amount of the at least one bioactive agent can be released with time from the invention polymer composition, including those in a biodegradable internal fixation device, stent, or dialysis shunt, or in a depot formed from particles thereof introduced in vivo. The suitable and effective amount of the bioactive agent will typically depend, e.g., on the specific alkylene di-acid-containing PEA polymer and type of particle or polymer/bioactive agent linkage, if present. Typically, up to about 100% of the bioactive agent(s) can be released from the invention polymer composition in vivo. Specifically, up to about 90%, up to 75%, up to 50%, or up to 25% thereof can be released from the polymer. Factors that typically affect the release rate from the polymer are the types of polymer/bioactive agent linkage, and the nature and amount of additional substances present in the formulation, as well as the chemical structure of the polymer itself.

In addition to humans, the invention alkylene di-acid-containing PEA polymer compositions, as well as particles and medical devices fabricated therefrom, are also intended for use in veterinary practice, including a variety of mammalian patients, such as pets (for example, cats, dogs, rabbits, and ferrets), farm animals (for example, swine, horses, mules, dairy and meat cattle) and race horses.

The compositions used in the invention devices and methods of delivery may comprise an "effective amount" of one or more backbone bioactive agent(s) and optional bioactive agents of interest. That is, an amount of a bioactive agent will be incorporated into the polymer that will produce a sufficient therapeutic or palliative response in order to prevent, reduce or eliminate symptoms. The exact amount necessary will vary, depending on the subject to which the composition is being administered; the age and general condition of the subject; the capacity of the subject's immune system, the degree of therapeutic or palliative response desired; the severity of the condition being treated or investigated; the particular bioactive agent selected and mode of administration of the composition, among other factors. An appropriate effective amount can be readily determined by one of skill in the art. Thus, an "effective amount" will fall in a relatively broad range that can be determined through routine trials. For example, for purposes of the present invention, an effective amount will typically range from about 1 µg to about 100 mg, for example from about 5 µg to about 1 mg, or about 10 µg to about 500 µg of the bioactive agent delivered.

The following examples are meant to illustrate, but not to limit the invention.

EXAMPLE 1

Synthesis of Invention PEAs

As the first stage of synthesis, a variety of new diester-diacids (or alkylene-dicarboxylates) of structural formula (III) have been fabricated by interaction of diols with cyclic aliphatic five or six-member anhydrides, such as maleic, succinic and glutaric anhydrides. The general scheme of alkylene-dicarboxylate synthesis is depicted in reaction Scheme 2 below:

Scheme 2

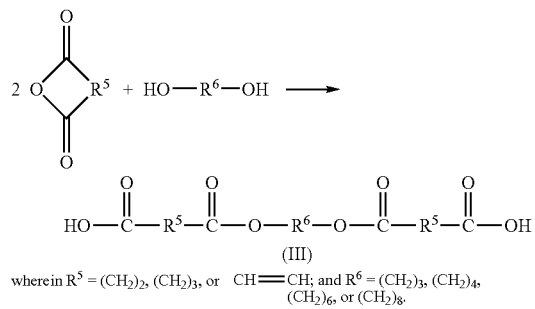

wherein $R^5 = (CH_2)_2, (CH_2)_3,$ or $CH=CH;$ and $R^6 = (CH_2)_3, (CH_2)_4, (CH_2)_6,$ or $(CH_2)_8$.

As the second stage of synthesis, various active di-(p-nitrophenyl) esters of alkylene-dicarboxylates of structural formula VI have been fabricated. The reaction was accomplished by interaction of di-acids formed in the first stage (Formula III) with p-nitrophenol in the presence of different condensing agents.

wherein $R^5$ can be selected from $(CH_2)_2, (CH_2)_3, CH=CH;$ and $R^6$ can be selected from $(CH_2)_3, (CH_2)_4, (CH_2)_6,$ and $(CH_2)_8$.

As the third stage of synthesis, the invention poly(ester amides) were synthesized by solution active polycondensation of compounds of Formula VI with bis(α-aminoacid)-diol-diester monomers in N,N'-dimethyl formamide in the presence of triethylamine as an acid acceptor, according to reaction Scheme 3 below, to yield the invention PEA composition described by structural formula (I):

Scheme 3

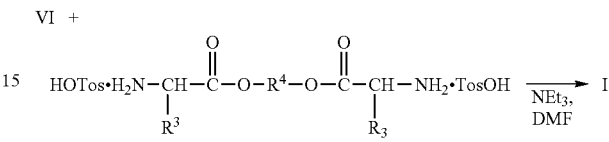

EXAMPLE 2

Monomer Synthesis
1. Synthesis of α,ω-alkylene Dicarboxylates of Structural Formula III.

Diester-diols derived from five-member anhydrides: alkylene-disuccinates (or O,O'-bis-succinyl diols of structural Formula III, where $R^5=(CH_2)_2$) and alkylene-dimaleates (where $R^5=$(cis-CH=CH)) can be prepared as follows.

Interaction of succinic and maleic anhydrides with diols according to Scheme 2 was carried out in refluxed benzene or toluene without using any catalyst. This procedure is illustrated by synthesis of 1,6-hydroxyhexyl-disuccinate as shown in reaction Scheme 4 below:

Scheme 4

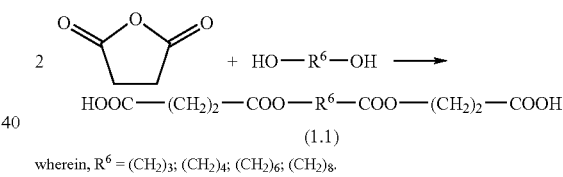

wherein, $R^6 = (CH_2)_3; (CH_2)_4; (CH_2)_6; (CH_2)_8$.

Diester-di-acids were purified by re-crystallization from benzene. Their yields are rather high and elemental analysis coincides well with calculated values, as shown in Table 1. Products were also characterized by Fourier Transform Infrared (FTIR) Spectroscopy and a typical spectrum of a diester-di-acid for compound 1,6-hydroxyhexyl-disuccinate, which is shown in FIG. 1, is in accordance with the assumed structure.

The experimentally determined acid numbers (in Table 1 below) of the invention di-acid-diesters are in good accordance with calculated values. Acid numbers were determined by using bromthymol blue (titration point at close to neutral pH 7) as an indicator for the titration of compound III with a solution of 0.1 N NaOH in water.

Data of elemental analysis are also in good accordance with the assumed structures.

(Formula VI)

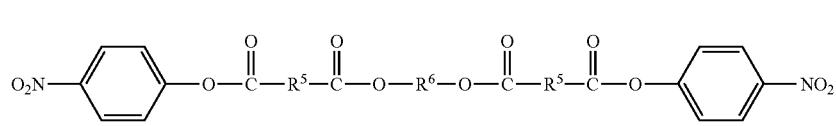

TABLE 1

Characteristics of synthesized alkylene-dicarboxylates III:

| # | Diester diacid (III) R$^5$ | R$^6$ | Yield, [%] | M.p. [°C.] | Acid Number, Found/ Calculated | Gross Formula (mol. weight) | Elemental analysis Found/ Calculated C | H |
|---|---|---|---|---|---|---|---|---|
| 1.1 | (CH$_2$)$_2$ | (CH$_2$)$_3$ | 75 | 170-5 | 406.16 / 403.22 | C$_{11}$H$_{16}$O$_8$ (276.24) | 47.76 / 47.83 | 5.68 / 5.84 |
| 1.2 | (CH$_2$)$_2$ | (CH$_2$)$_4$ | 80 | 112-4 | 386.54 / 343.93 | C$_{12}$H$_{18}$O$_8$ (290.27) | 49.72 / 49.65 | 6.23 / 6.25 |
| 1.3 | (CH$_2$)$_2$ | (CH$_2$)$_6$ | 83 | 107-9 | 352.47 / 3471.18 | C$_{14}$H$_{22}$O$_8$ (318.32) | 52.87 / 52.82 | 6.95 / 6.97 |
| 1.4 | (CH$_2$)$_2$ | (CH$_2$)$_8$ | 64 | 100-2 | 323.92 / 314.16 | C$_{16}$H$_{26}$O$_8$ (346.37) | 55.51 / 55.48 | 7.53 / 7.57 |
| 1.5 | (CH=CH) | (CH$_2$)$_3$ | 38 | 130-1 | — | C$_{11}$H$_{12}$O$_8$ (272.21) | — | — |
| 1.6 | (CH=CH) | (CH$_2$)$_4$ | 77 | 82-4 | — | C$_{12}$H$_{14}$O$_8$ (286.23) | 50.57 / 50.53 | 4.90 / 4.92 |
| 1.7 | (CH=CH) | (CH$_2$)$_6$ | 78 | 104-6 | — | C$_{14}$H$_{18}$O$_8$ (314.29) | 53.53 / 53.50 | 5.75 / 5.77 |
| 1.8 | (CH=CH) | (CH$_2$)$_8$ | 65 | 101-3 | — | C$_{16}$H$_{22}$O$_8$ (342.34) | — | — |
| 1.9 | (CH$_2$)$_3$ | (CH$_2$)$_4$ | 56 | 69-71 | 352.47 / 349.44 | C$_{14}$H$_{22}$O$_8$ (318.32) | 52.520 / 52.82 | 7.14 / 6.97 |
| 1.10 | (CH$_2$)$_3$ | (CH$_2$)$_6$ | 78 | 76-78 | 323.90 / 316.60 | C$_{16}$H$_{26}$O$_8$ (346.38) | 55.24 / 55.48 | 7.34 / 7.57 |
| 1.11 | (CH$_2$)$_3$ | (CH$_2$)$_8$ | 50 | 84-85 | 299.65 / 296.22 | C$_{18}$H$_{30}$O$_8$ (374.43) | 57.56 / 57.74 | 8.38 / 8.08 |

EXAMPLE 3

Unsaturated α,ω-alkylene dicarboxylates based on maleic acid (compounds 1.5-1.8 in Table 1) afford a new avenue to synthesis of unsaturated poly(ester-amides) (UPEAs)—a new class of biodegradable polyamides.

Synthesis of α,ω-alkylene-diglutarates (Where R$^5$=(CH$_2$)$_3$) of Structural Formula III Synthesis of di-acid-diesters on the basis of six member glutaric anhydride and α,ω-diols was carried out in a manner similar to that shown in reaction Scheme 5 below, or in general Scheme 2 herein:

Scheme 5

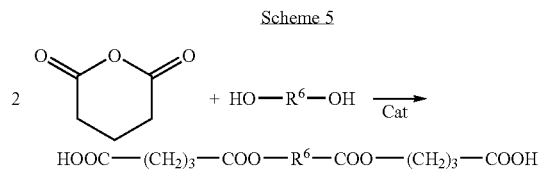

wherein, R$^6$ is selected from (CH$_2$)$_4$, (CH$_2$)$_6$, or (CH$_2$)$_8$.

Initial attempts to obtain the anticipated product by interaction of 2 moles of glutaric anhydride with 1 mole of diol in refluxed benzene or toluene without any catalyst were unsuccessful and showed no conversion. The intended products were obtained in nearly quantitative yields only after using p-toluenesulfonic acid as a catalyst, a result that indicates much lower reactivity of six-membered anhydrides than five-member analogues succinic and maleic anhydrides. Yields, elemental composition and other characteristics of synthesized product compounds are summarized in Table 1.

In a typical procedure, 0.05 mole of the diol and 12.97 g (0.11 mole) of glutaric anhydride (Aldrich Chemicals) were placed in a round-bottomed flask equipped with a stirrer and condenser, and 0.1 g of p-toluenesulfonic acid and 32 mL of benzene were added at room temperature. The flask was placed in a silicon oil bath and the benzene was refluxed for 6 h. The initially heterogeneous reaction mixture became homogeneous upon heating, and the reaction proceeded homogeneously in refluxed benzene. However, after cooling to room temperature, the product crystallized. The white solid precipitate was filtered off, dried and recrystallized from benzene. Yields of the product compounds after recrystallization were in a range of 50%-78%.

EXAMPLE 4

Synthesis of di-p-nitrophenyl Esters of α,ω-alkylene Dicarboxylates of Formula VI Two different procedures were applied for transferring new di-acids into di-(p-nitrophenyl)-esters (of Formula VI): In one procedure, saturated alkylene-dicarboxylates (where R$^5$= (CH$_2$)$_2$ or (CH$_2$)$_3$) were condensed with di-p-nitrophenol in the presence of thionyl chloride/pyridine as a condensing agent, according to Scheme 6:

Scheme 6

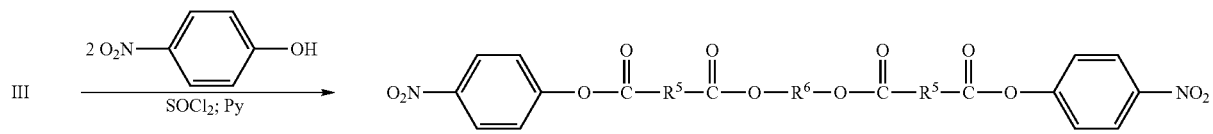

Figure 2:
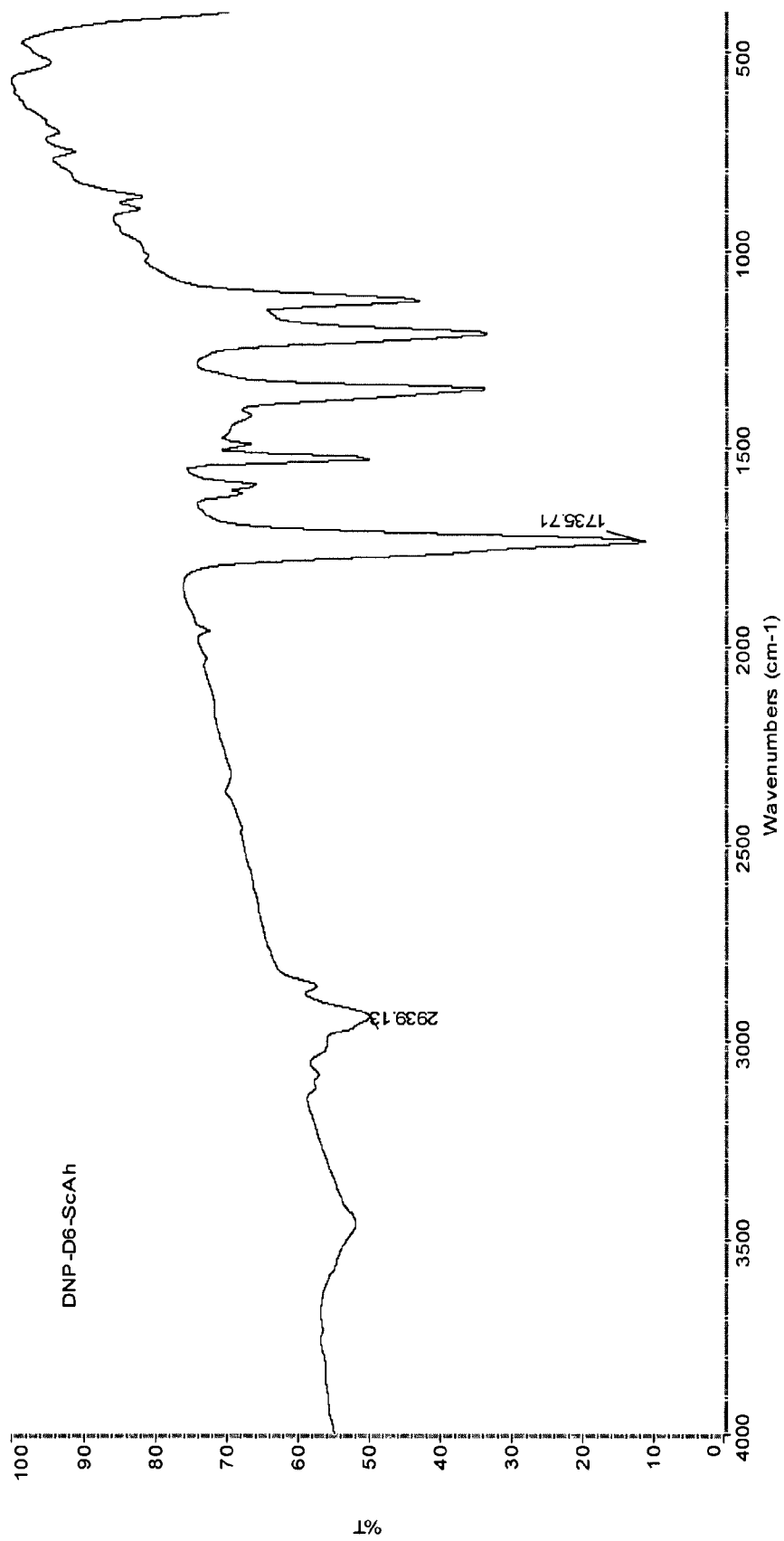
FIG. 2 is a graph showing the FTIR spectra of an active diester of structural Formula VI (Compound 2.2 of Table 2).

Obtained products were re-crystallized from ethanol. The yields and characteristics are summarized in Table. 2. FTIR spectra of di-p-nitrophenolates confirmed the assumed structure (FIG. 2).

TABLE 2

Characteristics of active diesters VI.

| # | Active di-esters (VI) $R^5$ | $R^6$ | Yield, [%] | M.p. [° C.] | Gross Formula [Mol. Weight] | Elemental analysis Found/Calculated C | H | N |
|---|---|---|---|---|---|---|---|---|
| 2.1 | $(CH_2)_2$ | $(CH_2)_4$ | 55 | 72-4 | $C_{24}H_{24}N_2O_{12}$ (532.45) | 54.58 / 54.14 | 4.43 / 4.54 | 5.29 / 5.26 |
| 2.2 | $(CH_2)_2$ | $(CH_2)_6$ | 78 | 82-4 | $C_{26}H_{28}N_2O_{12}$ (560.51) | 55.66 / 55.71 | 5.15 / 5.04 | 5.07 / 5.00 |
| 2.3 | $(CH_2)_2$ | $(CH_2)_8$ | 65 | 67-1 | $C_{28}H_{32}N_2O_{12}$ (588.20) | 57.10 / 57.14 | 5.39 / 5.48 | 4.74 / 4.76 |
| 2.4 | CH=CH | $(CH_2)_6$ | 70 | 116-7 | $C_{26}H_{26}N_2O_{12}$ (558.49) | 55.88 / 55.91 | 4.41 / 4.69 | 5.04 / 5.02 |

Unsaturated diester-di-acid based on maleic acid (compound 2.4, Table 2) also was transformed into a di-(p-nitrophenyl) ester. For unsaturated diester-di-acids, the combination of condensing reagents thionyl chloride/pyridine was found unsuitable because undesirable side reactions occurred, resulting in dark tar. A complex of trifluoracetic anhydride/triethylamine was found to be more satisfactory as a condensing agent. The reaction was carried out as described in reaction Scheme 7 below:

Scheme 7

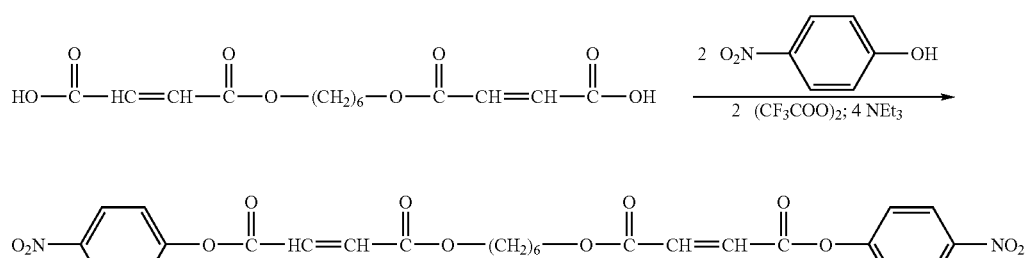

The synthesis of unsaturated active diester of structural Formula VI (in fact, tetraester) was carried out in chlorobenzene at room temperature (according to Scheme 5). After 6 h of stirring, the reaction mixture was evaporated to dryness and obtained solid product washed with water acidified (pH 2-3) with hydrochloric acid directly on the glass filter, the residual solid product was dried and recrystallized from absolute ethanol. Yield of purified diester (white crystals) Compound 2.4 was 70%, melting point 116-117° C.

EXAMPLE 5

PEA Synthesis

Figure 3:
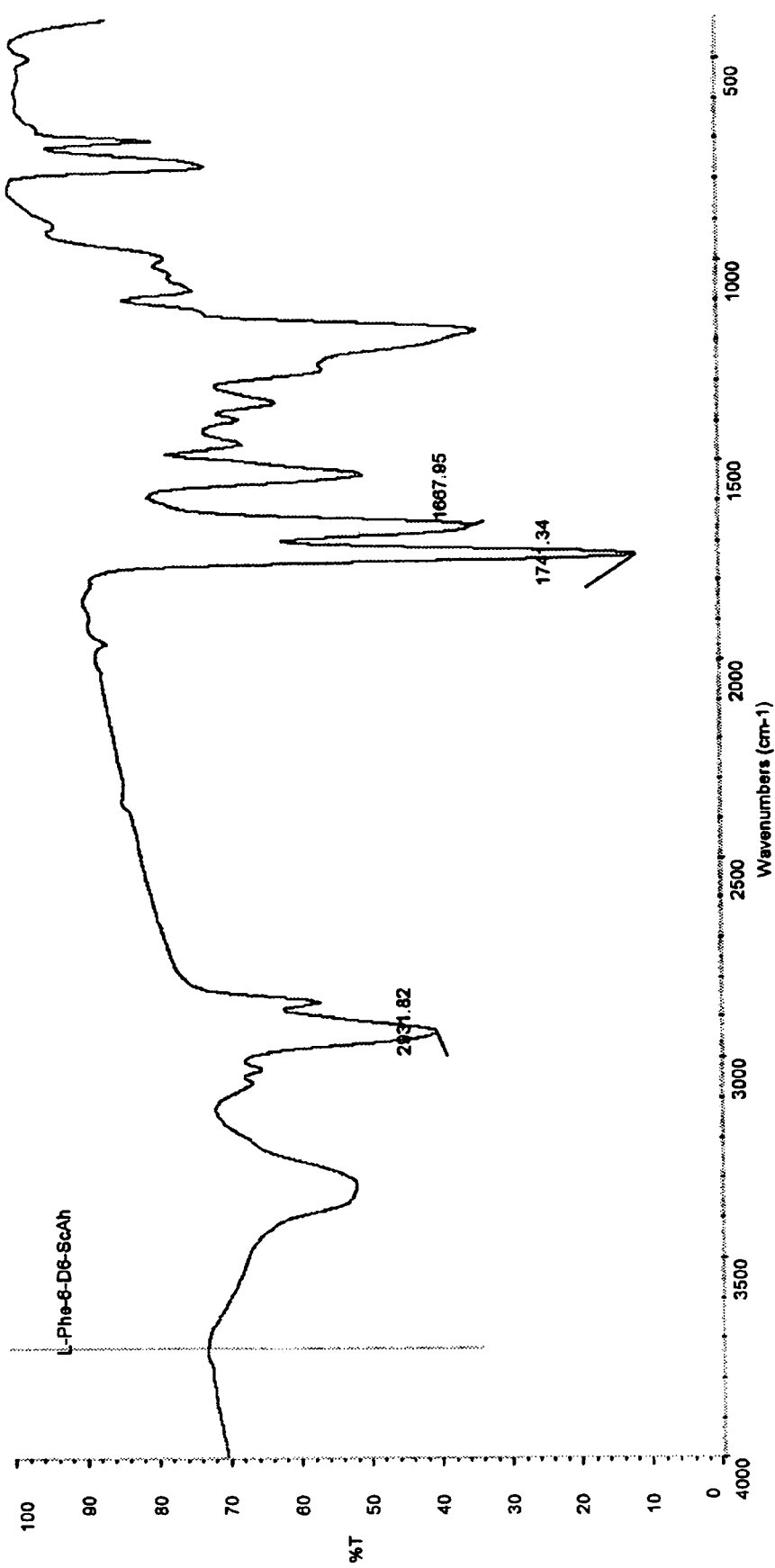
FIG. 3 is a graph showing

Poly(ester amides) were synthesized under the conditions of solution active polycondensation in DMA using triethylamine as an acid acceptor, according to general Scheme 2. Polycondensation with compound 2.2, of Table 2, was carried out at mild temperatures (from room temperature to 45° C.) to avoid succinimide formation (cyclization) and chain termination. The resulting reaction solutions were poured into water, precipitated polymers were washed thoroughly with an acetone/water (50/50 v/v) mixture, until a negative test for the presence of p-nitrophenol was achieved, and dried at 40° C. under reduced pressure. High-molecular-weight PEAs having good film-forming properties were synthesized at those conditions, as shown by the results summarized in Table 3. The results of elemental analysis of selected samples (Table. 3), and FTIR spectra (FIG. 3) are in accordance with the expected structure.

TABLE 3

Characteristics of PEAs, of formula V, (where $R^6 = (CH_2)_2$; $R^3 = CH_2C_6H_5$, $R^4 = (CH_2)_6$.)

| PEA (I) # | $R^5$ | Yield, in % | Gross formula (formula weight) | $M_w$ | $M_n$ | $M_w/M_n$ | Elemental analysis Found/Calculated C | H | N |
|---|---|---|---|---|---|---|---|---|---|
| 3.1 | $(CH_2)_4$ | 89 | $C_{38}H_{50}N_2O_{10}$ (694.81) | 42,500 | 26,500 | 1.61 | 65.22 / 65.59 | 7.38 / 7.25 | 4.34 / 4.03 |
| 3.2 | $(CH_2)_6$ | 93 | $C_{40}H_{54}N_2O_{10}$ (694.81) | 46,300 | 26,900 | 1.72 | — | — | — |
| 3.3 | $(CH_2)_8$ | 90 | $C_{42}H_{58}N_2O_{10}$ (694.81) | 42,200 | 26,400 | 1.60 | — | — | — |

For synthesis of PEA based on an unsaturated bis-electrophilic monomer of structural Formula VI, di-p-toluenesulfonic acid salt of bis-(L-phenylalanine)-1,6-hexylene was chosen as a bis-nucleophilic partner according to reaction Scheme 8 below:

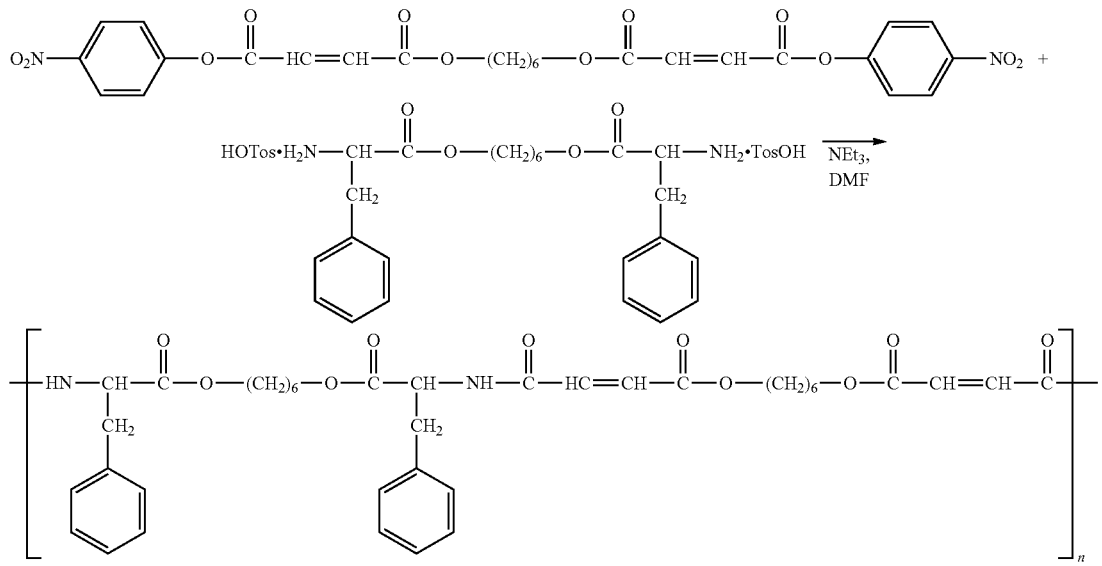

Scheme 8

The polycondensation was carried out in various solvents (N,N'-dimethylacetamide, acetone, chlorobenzene) both at room temperature and upon cooling to −5° C.; however, in all cases regardless of the reaction temperature and nature of the solvent used, cross-linkage and formation of insoluble polymers could not be avoided, presumably due to the interaction of terminal amino groups of the growing macro-chains with double bonds of maleic acid residue in the polymeric backbones.

EXAMPLE 6

PEA Hydrolysis Study
Biodegradation (General Procedure)

Invention PEA compositions were subjected to in vitro enzymatic hydrolysis. For this experiment, polymer films were prepared and degradation kinetics were studied by weight loss using the following procedure.

Circular polymer disks with d=4 cm, weight of 500-600 mg were placed into glass vessels containing 10 mL of 0.2 M phosphate buffer solution of pH=7.4, either with 4 mg of an enzyme—(α-chymotrypsin or lipase) or without enzyme. The glass vessels containing the buffer solution were maintained at 37° C. The discs were removed from the buffer solutions every 24 hr and dried to constant weight. The weight change per unit surface area of the sample was calculated (in mg/cm$^2$). Total duration of the biodegradation experiments was 120 hours.

For this experiment a PEA of structural Formula V)—composed of hexanediol ($R^4=R^6=(CH_2)_6$), succinic acid ($R^5=(CH_2)_2$), and L-phenylalanine ($R^3=CH_2C_6H_5$) —was subjected to in vitro biodegradation according to the above-described procedure.

TABLE 3

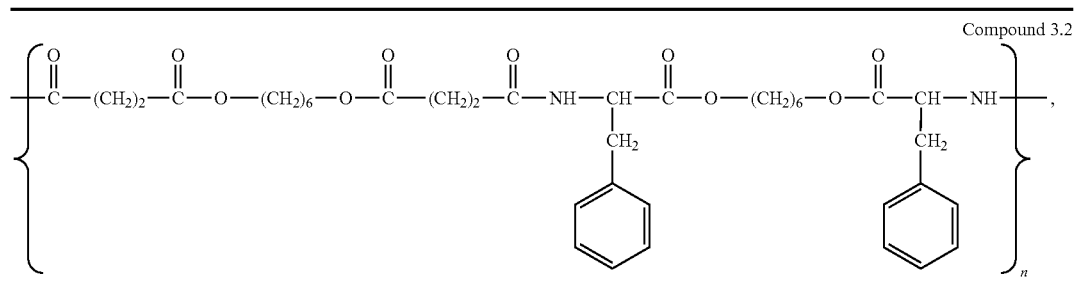

Compound 3.2

Figure 4:
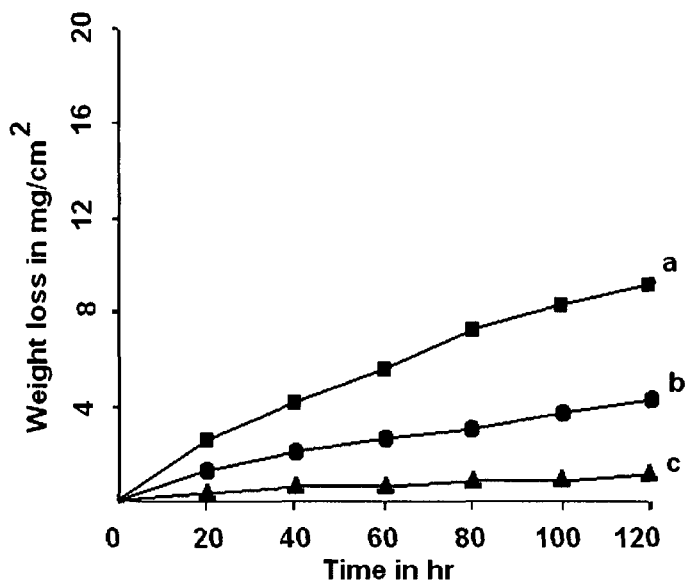
FIG. 4 is a graph showing the in vitro biodegradation (weigh loss in mg/cm²) of invention succinic acid-based PEA (Compound 3.2 of Table 3) in 0.2 M phosphate buffer (pH=7.4, t=25° C.) under the action of a) lipase (4 mg/10 mL), b) α-chymotrypsin (4 mg/10 mL), and c) in pure buffer.
Figure 5:
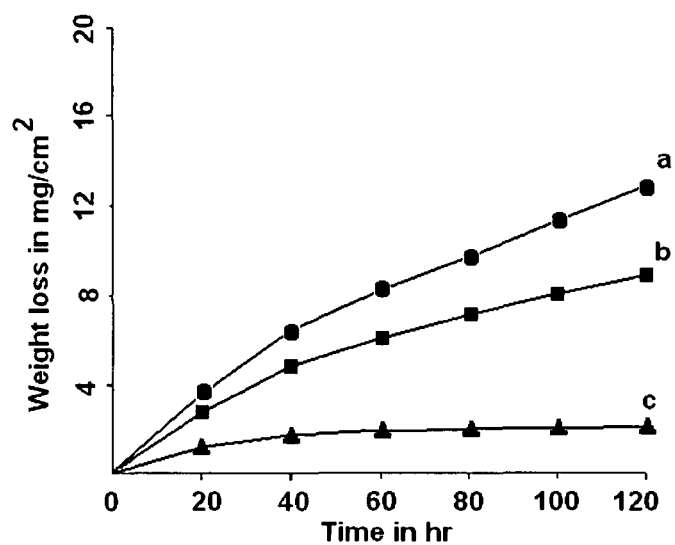
FIG. 5 is a graph showing the in vitro biodegradation (weigh loss in mg/cm²) of sebacic acid-based PEA 8-L-Phe-6 in 0.2 M phosphate buffer (pH=7.4, t=25° C.) under the action of a) α-chymotrypsin (4 mg/10 mL) and b) lipase (4 mg/10 mL), and c) in pure buffer.

Obtained results (FIG. 4) show the invention PEA above underwent in vitro biodegradation at a rather high rate, comparable to biodegradation rates of known PEA based on sebacic acid, PEA 8-L-Phe-6 (Formula I, where $R^1=(CH_2)_8$; $R^3=CH_2C_6H_5$; and $R^4=(CH_2)_6$)—one of the fastest biodegradable AAB-PEAs (see the degradation profile in FIG. 5). By contrast, virtually no substantial weight loss was observed in pure buffer solution for the invention PEA (Compound 3.2 of Table 3).

It should be noted that with sebacic acid-based PEA, α-chymotrypsin is more active than lipase; whereas with invention Compound 3.2 (Table 3), lipase has greater degradation activity, which greater activity presumably is connected with a higher concentration of ester bonds in the polymer backbone per unit in the invention sebacic-acid-based PEA compositions than in the earlier known succinic acid-based PEA composition.

GPC analysis of PEAs before and after 120 hours of enzymatic hydrolysis was also conducted. Average molecular weight ($M_W$) characteristics summarized in Table 4 below show that in all cases, regardless of the nature of the enzyme or its presence, the molecular weight of invention PEA (Compound 3.2) decreased nearly twice as much as that control initial polymer sample.

In the same conditions, sebacic acid-based PEA 8-L-Phe-6 shows significant degradation (up to 50% weight loss), but without compromising its bulk properties, as shown by Mw characteristics summarized in Table 5 below. These results indicate that PEA Compound 3.2 underwent bulk erosion; whereas the sebacic acid-based polymer, PEA 8-L-Phe-6, degraded by a mechanism of surface degradation.

TABLE 4

Mw* characteristics of PEA 3.2 after 120 h biodegradation.

| PEA 3.2 | Mw | Mn | Mw/Mn |
|---|---|---|---|
| Initial polymer (control) | 27,500 | 18,100 | 1.51 |
| α-Chymotrypsin | 15,500 | 10,100 | 1.54 |
| Lipase | 18,000 | 10,900 | 1.65 |
| Buffer | 16,900 | 10,500 | 1.62 |

*GPC results were carried out in N,N-diemthylacetamide (PEG standards)

TABLE. 5

Mw characteristics of PEA 8-L-Phe-6 after 50% biodegradation.

| PEA 8-L-Phe-6 | Mw | Mn | Mw/Mn |
|---|---|---|---|
| Initial polymer (control) | 58600 | 30500 | 1.92 |
| α-Chymotrypsin | 58600 | 32000 | 1.82 |
| Lipase | 58600 | 31200 | 1.87 |
| Buffer | 58200 | 30700 | 1.92 |

Decreasing of average molecular weights (Mw) of the samples, as was expected, can be explained by intramolecular "self-catalysis" of succinic acid derivatives.

All publications, patents, and patent documents are incorporated by reference herein, as though individually incorporated by reference. The invention has been described with reference to various specific and preferred embodiments and techniques. However, it should be understood that many variations and modifications might be made while remaining within the spirit and scope of the invention.

Although the invention has been described with reference to the above examples, it will be understood that modifications and variations are encompassed within the spirit and scope of the invention. Accordingly, the invention is limited only by the following claims.

That which is claimed is:

1. A biodegradable polymer composition comprising at least one (PEA) polymer have a structure according to formula (IV):

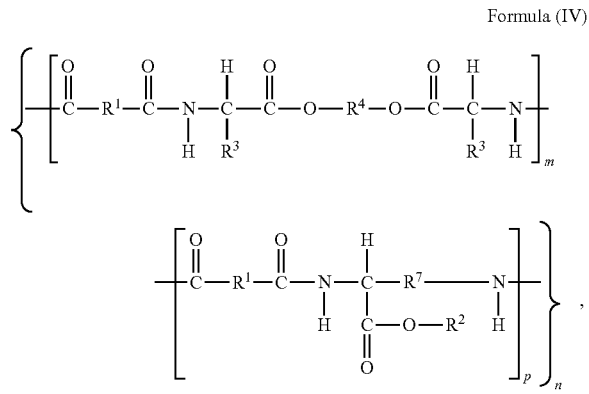

Formula (IV)

wherein
n ranges from about 5 to about 150,
m ranges about 0.1 to 0.9;
p ranges from about 0.9 to 0.1;
$R^1$ is independently selected from residues of α,ω-alkylene dicarboxylates of structural formula (III)

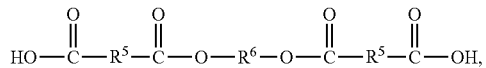

Formula (III)

optionally in combination with $(C_2\text{-}C_{20})$ alkylene;
$R^5$ and $R^6$ in Formula (III) are independently selected from $(C_2\text{-}C_{12})$ alkylene or $(C_2\text{-}C_{12})$ alkenylene;
each $R^2$ is independently hydrogen, $(C_1\text{-}C_{12})$alkyl, $(C_6\text{-}C_{10})$aryl or a protecting group;
the $R^3$s in individual m monomers are independently selected from hydrogen, $(C_1\text{-}C_6)$alkyl, $(C_2\text{-}C_6)$alkenyl, $(C_2\text{-}C_6)$alkynyl, $(C_6\text{-}C_{10})$aryl$(C_1\text{-}C_6)$alkyl, and —$(CH_2)_2S(CH_3)$;
$R^4$ is independently selected from $(C_2\text{-}C_{20})$alkylene, $(C_2\text{-}C_{20})$ alkenylene, $(C_2\text{-}C_8)$alkyloxy, $(C_2\text{-}C_{20})$alkylene, bicyclic-fragments of 1,4:3,6-dianhydrohexitols of structural formula (II)

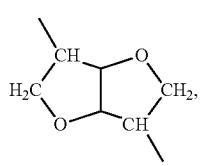

Formula (II)

and residues of saturated or unsaturated therapeutic diols and combinations thereof; and
$R^7$ is independently selected from $(C_2\text{-}C_{20})$ alkyl or $(C_2\text{-}C_{20})$ alkenyl.

2. The composition of claim 1, wherein at least one of the $R^1$s in an n or m unit is independently selected from residues of αω-alkylene dicarboxylates of formula (III), wherein $R^5$ and $R^6$ in Formula (III) are independently selected from $(C_2\text{-}C_{12})$alkylene and $(C_2\text{-}C_{12})$ alkenylene, and wherein at least one of the $R^1$s in the n or m unit is $(C_2\text{-}C_{20})$ alkylene.

3. The composition of claim 1, wherein R5 in Formula (III) is (CH=CH); and R6 is (CH2)3, (CH2)4, (CH2)6, or (CH2)8.

4. The composition of claim 1, wherein at least one R1 is 1,4-hydroxybutyl disuccinate, 1,3-hydroxypropyl dimalonate or 1,6-hydroxyhexyl diglutarate.

5. The composition of claim 1, wherein at least one R1 is a saturated or unsaturated residue of a therapeutic di-acid.

6. The composition of claim 1, wherein the R3 s in an n or m monomer are independently selected from hydrogen, CH2-CH(CH3)2, CH3, CH(CH3)2, CH(CH3)-CH2-CH3, CH2-C6H5, or (CH2)2SCH3.

7. The composition of claim 1, wherein from about 0.1 part to about 0.9 part of R4 is 1,4:3,6-dianhydrohexitol.

8. The composition of claim 1, wherein the polymer has a molecular weight in the range from about 15,000 Da to about 600,000 Da.

9. The composition of claim 1, wherein the composition further comprises an effective amount of at least one bioactive agent dispersed in the polymer.

10. The composition of claim 9, wherein the composition includes from about 5 to about 150 molecules of the bioactive agent per polymer molecule chain.

11. The composition of claim 9 wherein the at least one bioactive agent is covalently bonded to the polymer.

12. The composition of claim 9, wherein there are at least two bioactive agents dispersed in the composition.

13. The composition of claim 1, wherein formula (III):

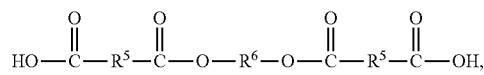

Formula (III)

$R^5$ is selected from $(CH_2)_2$, $(CH_2)_3$, and CH=CH; and $R^6$ is selected from $(CH_2)_3$, $(CH_2)_4$, $(CH_2)_6$, and $(CH_2)_8$.

* * * * *